(12) United States Patent
Woltering et al.

(10) Patent No.: US 6,608,049 B2
(45) Date of Patent: Aug. 19, 2003

(54) INDAZOLES

(75) Inventors: Michael Woltering, Wuppertal (DE); Helmut Haning, Milford, CT (US); Gunter Schmidt, Wuppertal (DE); Josef Pernerstorfer, Wuppertal (DE); Hilmar Bischoff, Wuppertal (DE); Axel Kretschmer, Wuppertal (DE); Verena Vöhringer, Wuppertal (DE); Christiane Faeste, Haan (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/956,566

(22) Filed: Sep. 18, 2001

(65) Prior Publication Data

US 2002/0193610 A1 Dec. 19, 2002

(30) Foreign Application Priority Data

Sep. 18, 2000 (DE) .......................... 100 46 029

(51) Int. Cl.[7] .................. A61K 31/4162; C07D 231/56
(52) U.S. Cl. .................. 514/186; 548/304.4; 548/306.4
(58) Field of Search ........................ 548/306.4, 304.4; 514/186

(56) References Cited

FOREIGN PATENT DOCUMENTS

| DE | 2032171 | | 1/1972 |
|---|---|---|---|
| EP | 0188351 | | 7/1986 |
| EP | 0580550 | | 1/1994 |
| GB | 1335 603 | * | 10/1973 |
| WO | 9857919 | | 12/1998 |
| WO | 9926966 | | 6/1999 |
| WO | 0002850 | | 1/2000 |
| WO | 0005216 | | 3/2000 |
| WO | 0051971 | | 9/2000 |
| WO | 0058279 | | 10/2000 |
| WO | 0153268 | | 7/2001 |

OTHER PUBLICATIONS

Yokoyama, N., Walker, G. N., Main, A. J., Stanton, J. L., Morrissey, M. M., Boehm, C., Engle, A., Neubert, A. D., Wasvary, J. M., Stephan, Z. F., Steele, R. E., "Synthesis and Structure—Activity Relationship of Oxamic Acid and Acetic Acid Derivatives Related to L–Thyronine", J. Med. Chem., 38: 695–707 (1995).

* cited by examiner

Primary Examiner—Joseph K. McKane
Assistant Examiner—Rebecca Anderson
(74) Attorney, Agent, or Firm—Susan M. Pellegrino

(57) ABSTRACT

The invention relates to new indazole derivatives, processes for their preparation, and their use in medicaments.

17 Claims, No Drawings

INDAZOLES

The invention relates to new indazole derivatives, processes for their preparation, and their use in medicaments.

EP-A-580 550 describes oxamic acid derivatives which have cholesterol-lowering properties in mammals. The pharmacological characteristic emphasized is the reduction of plasma cholesterol, in particular of LDL cholesterol. Cholesterol-lowering actions are also described in EP-A-188 351 for certain diphenyl ethers having thyroid hormone-like actions, which differ clearly in their chemical structure from the compounds according to the invention.

Indazoles which are connected to a substituted phenyl ring in the 5 position via a bridge member have been disclosed (JP-A-08022109, JP-A-59098060). No thyroid hormone-like properties are described for these 5-substituted indazoles.

An object of the invention is the provision of novel compounds having improved actions, in particular pharmaceutical actions.

It has now been found that compounds of the general formula (I),

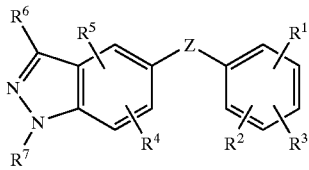

in which

Z represents O, S, $CH_2$, CHF or $CF_2$, $R^1$ and $R^2$ are identical or different and represent hydrogen, halogen, $(C_1-C_6)$-alkyl, $CF_3$, $CHF_2$, $CH_2$, $CH_2F$, vinyl or $(C_3-C_7)$-cycloalkyl, where at least one of the two substituents is not equal to hydrogen and is in the ortho position relative to the bridge bond, $R^3$ represents a head group having an optionally derivatized carboxyl radical, preferably a group of the formula $$A\text{-}(CH_2)_n\text{---}(CO)_m\text{---}R^8,$$

in which

A represents $CH_2$, O, S, CO or $NR^9$, in which $R^9$ denotes hydrogen, $(C_1-C_6)$-alkyl or $(C_3-C_8)$-cycloalkyl or represents the group —$(CH_2)_n$—$(CO)_m$—O—$(C_1-C_4)$-alkyl, n represents the numbers 0 to 3, m represents the number 0, 1 or 2, $R^8$ represents hydrogen, hydroxyl, $OR^{10}$, $NR^{11}R^{12}$, $(C_1-C_8)$-alkyl, $(C_3-C_8)$-cycloalkyl, $(C_6-C_{10})$-aryl, or a saturated, unsaturated or aromatic 5- to 10-membered heterocycle having up to four identical or different heteroatoms from the series S, O and/or N, where the abovementioned radicals are optionally substituted by one, two or three, identical or different substituents from the group halogen, hydroxyl, cyano, nitro, amino, $CF_3$, $(C_1-C_6)$-alkyl, $(C_1-C_6)$-alkoxy, $(C_3-C_8)$-cycloalkyl, —OCO—$R^{13}$, —CO—O—$R^{14}$, —CO—$NR^{15}R^{16}$, —$NHCOR^{17}$ or $NHCOOR^{17}$, where $R^{10}$, $R^{11}$, $R^{12}$, $R^{13}$, $R^{14}$, $R^{15}$, $R^{16}$ and $R^{17}$ are identical or different and in each case represent hydrogen, phenyl, benzyl, $(C_1-C_6)$-alkyl, $(C_1-C_6)$-alkoxy or $(C_3-C_8)$-cycloalkyl, which for their part are optionally mono- or polysubstituted by halogen, hydroxyl, amino, $(C_1-C_4)$-alkoxy, —CO—O$(C_1-C_4)$-alkyl, —NH—CO—O $(C_1-C_4)$-alkyl, —O—CO—$(C_1-C_4)$-alkyl, a heterocycle or optionally halogen- or hydroxyl-substituted phenyl, $R^4$ and $R^5$ are identical or different and in each case represent hydrogen, hydroxyl, halogen, cyano, nitro, $(C_1-C_4)$-alkyl, or the radical of the formula $NR^{18}R^{19}$, where $R^{18}$ and $R^{19}$ have the meaning indicated for $R^{10}$ and can be identical to or different from this substituent, $R^6$ represents halogen or has the meaning indicated for $R^8$ and is identical to or different from this substituent or represents the radical

in which $R^{20}$ and $R^{21}$ together represent oxygen, or are each identical or different and represent hydrogen, halogen, hydroxy, $(C_1-C_6)$-alkyl, $(C_1-C_6)$-alkoxy or the radical —$NR^{15}R^{16}$ and $R^{22}$ has the meaning of $R^8$ and is identical to or different from this, $R^7$ represents hydrogen or an acyl group which can be cleaved under physiological conditions with formation of an NH function, preferably hydrogen or acetyl, and their salts, preferably the compounds which are mono- or di-ortho-substituted in the phenyl moiety and have a substituent in the 3 position in the indazole ring, show a pharmacological action and can be used as medicaments or for the production of pharmaceutical formulations.

Heterocycles which may preferably be mentioned in the definition of $R^8$ or of $R^6$ are:

a 5- to 8-membered saturated, partly unsaturated or aromatic optionally benzo-fused heterocycle having up to 4 heteroatoms from the series S, N and/or O, i.e. a heterocycle which can contain one or more double bonds and which is linked via a ring carbon atom or a ring nitrogen atom. Examples which may be mentioned are: tetrahydrofur-2-yl, tetrahydrofur-3-yl, pyrrolidin-1-yl, pyrrolidin-2-yl, pyrrolidin-3-yl, pyrrolin-1-yl, piperidin-1-yl, piperidin-3-yl, 1,2-dihydropyridin-1-yl, 1,4-dihydropyridin-1-yl, piperazin-1-yl, morpholin-1-yl, azepin-1-yl, 1,4-diazepin-1-yl, furan-2-yl, furan-3-yl, pyrrol-1-yl, pyrrol-2-yl, pyrrol-3-yl, thienyl, thiazolyl, oxazolyl, imidazolyl, triazolyl, tetrazolyl, pyridyl, pyrimidyl, pyrazinyl, pyrimidinonyl, pyridazinonyl.

Those preferred from this list are: pyridyl, pyrimidyl, pyridazinyl, pyrimidinonyl, pyridazinonyl and thiophenyl.

Derivatized carboxyl radicals in the definition of the substituent $R^3$ preferably denote groups which can be broken down in the sense of a prodrug to the carboxylic acid or its salts, such as halides, anhydrides, esters or amides.

Alkyl in the context of the invention represents a straight-train or branched alkyl radical preferably having 1 to 15, 1 to 12, 1 to 10, 1 to 8, 1 to 6, 1 to 4 or 1 to 3 carbon atoms. A straight-chain or branched alkyl radical having 1 to 3 carbon atoms is preferred. The following may be mentioned by way of example and preferably: methyl, ethyl, n-propyl, isopropyl, n-, i-, s- or t-butyl, n-pentyl and n-hexyl.

Aryl in the context of the invention represents an aromatic radical preferably having 6 to 10 carbon atoms. Preferred aryl radicals are phenyl and naphthyl.

Cycloalkyl in the context of the invention represents a cycloalkyl group preferably having 3 to 8, 3 to 7 or 3 to 6 carbon atoms. The following may be mentioned by way of example and preferably: cyclopropyl, cyclobutyl, cyclopentyl, cyclohexyl and cycloheptyl.

Alkoxy in the context of the invention preferably represents a straight-chain or branched alkoxy radical having 1 to 6 carbon atoms. A straight-chain or branched alkoxy radical having 1 to 3 carbon atoms is preferred. The following may be mentioned by way of example and preferably: methoxy, ethoxy, n-propoxy, isopropoxy, t-butoxy, n-pentoxy and n-hexoxy.

Halogen in the context of the invention includes fluorine, chlorine, bromine and iodine. Fluorine, chlorine or bromine is preferred.

Depending on the substitution pattern, the compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can be converted into the stereoisomerically uniform constituents in a known manner.

Certain compounds can furthermore be present in tautomeric forms. This is known to the person skilled in the art, and compounds of this type are likewise encompassed by the scope of the invention.

The compounds according to the invention can also be present as salts. Physiologically acceptable salts are preferred in the context of the invention.

Physiologically acceptable salts can be salts of the compounds according to the invention with inorganic or organic acids. Preferred salts are those with inorganic acids such as hydrochloric acid, hydrobromic acid, phosphoric acid or sulphuric acid, or salts with organic carboxylic or sulphonic acids such as acetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Physiologically acceptable salts can likewise be salts of the compounds according to the invention with bases, such as metal or ammonium salts. Preferred examples are alkali metal salts (e.g. sodium or potassium salts), alkaline earth metal salts (e.g. magnesium or calcium salts), and also ammonium salts which are derived from ammonia or organic amines, such as ethylamine, di- or triethylamine, ethyldiisopropylamine, monoethanolamine, di- or triethanolamine, dicyclohexylamine, dimethylaminoethanol, dibenzylamine, N-methylmorpholine, dihydroabietylamine, 1-ephenamine, methylpiperidine, arginine, lysine, ethylenediamine or 2-phenylethylamine.

The compounds according to the invention can also be present in the form of their solvates, in particular in the form of their hydrates.

Preferred compounds of the general formula (I) are those in which

Z represents O, $CH_2$ or $CF_2$, $R^1$ and $R^2$ are identical or different and represent hydrogen, fluorine, chlorine, bromine, $(C_1-C_4)$-alkyl, $CF_3$, $CHF_2$, $CH_2F$, vinyl or $(C_3-C_6)$-cycloalkyl, where at least one of the two substituents is not equal to hydrogen and is in the ortho position relative to the bridge bond, in particular both substituents are not equal to hydrogen and both are in the ortho position, $R^3$ represents a head group having an optionally derivatized carboxyl radical, preferably a group of the formula

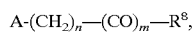

which is preferably in the para position relative to the bridge bond, in which

A represents $CH_2$, O or $NR^9$, in which $R^9$ denotes hydrogen, $(C_1-C_4)$-alkyl or $(C_3-C_7)$-cycloalkyl or represents the group $—(CH_2)_n—(CO)_m—O—(C_1-C_4)$-alkyl, n represents the number 0 or 1, m represents the number 1 or 2, $R^8$ represents hydrogen, hydroxyl, $OR^{10}$, $NR^{11}R^{12}$, $(C_1-C_8)$-alkyl $(C_3-C_8)$-cycloalkyl, $(C_6-C_{10})$-aryl, or a saturated, unsaturated or aromatic 5- to 10-membered heterocycle having up to four identical or different heteroatoms from the series S, O and/or N, where the abovementioned hydrocarbon radicals and heterocycles are optionally substituted by one, two or three identical or different substituents from the group halogen, hydroxyl, cyano, nitro, amino, $CF_3$, $(C_1-C_4)$-alkyl, $(C_1-C_4)$-alkoxy, $(C_1-C_4)$-alkoxyphenyl, $(C_3-C_8)$-cycloalkyl, $—O—CO—R^{13}$, $—CO—O—R^{14}$, $—CO—NR^{15}R^{16}$, $—NHCOR^{17}$ or $—NHCOOR^{17}$, where $R^{10}$, $R^{11}$, $R^{12}$, $R^{13}$, $R^{14}$, $R^{15}$, $R^{16}$ and $R^{17}$ are identical or different and each represent hydrogen, benzyl, $(C_1-C_6)$-alkyl or $(C_3-C_8)$-cycloalkyl, which for their part are optionally mono- or polysubstituted by fluorine, chlorine, hydroxyl, amino, $—CO—O—(C_1-C_4)$-alkyl, $—NH—CO—O(C_1-C_4)$-alkyl, $—O—CO—(C_1-C_4)$-alkyl, imidazolyl, hydroxyphenyl or $(C_1-C_4)$-alkoxy, $R^4$ and $R^5$ are identical or different and each represent hydrogen, halogen or $(C_1-C_4)$-alkyl, $R_6$ represents chlorine, fluorine, bromine or has the meaning indicated for $R^8$ and is identical to or different from this abovementioned substituent or represents the radical

in which $R^{20}$ and $R^{21}$ together represent oxygen, or are each identical or different and represent hydrogen, halogen, hydroxyl, $(C_1-C_4)$-alkyl, $(C_1-C_4)$-alkoxy or the radical $—NR^{15}R^{16}$ and $R^{22}$ has the meaning of $R^8$ and is identical to or different from this, $R^7$ represents hydrogen, and their salts.

Compounds of the general formula (I) of particular importance are those in which Z represents $CH_2$ or in particular oxygen, $R^1$ and $R^2$ are identical or different and represent methyl, ethyl, propyl, isopropyl, chlorine, bromine, $CF_3$, vinyl or cyclopropyl, where both substituents are in the ortho position to the bridge bond, R³ represents the group —O—(CH₂)ₙ—CO—R⁸ or preferably the group NR⁹—(CH₂)ₙ—(CO)ₘ—R⁸, which is each in the para position relative to the bridge bond, where R⁹ denotes —CH₂—CO—O—(C₁–C₄)-alkyl, substituted (C₁–C₄)-alkyl, (C₃–C₇)-cycloalkyl, —CO—CO—O—(C₁–C₄)-alkyl or in particular hydrogen, m represents the number 1 or in particular 2, n represents the number 1 or 0, R⁸ represents methyl, ethyl, n-propyl, isopropyl, n-, i-, s- or t-butyl, n-pentyl or n-hexyl, thiophenyl, pyridyl, or the groups —CH₂—O-benzyl, OR¹⁰ or NR¹¹R¹², where R¹⁰ represents hydrogen, or optionally hydroxyl-substituted straight-chain or branched alkyl having up to 7 carbon atoms, where R¹¹ and R¹² are identical or different and represent hydrogen, cyclopropyl, cyclobutyl, cyclopentyl, cyclohexyl, cycloheptyl, methoxy, ethoxy, n-propoxy, isopropoxy, t-butoxy, n-pentoxy, n-hexoxy or straight-chain or branched alkyl having up to 6 carbon atoms, where alkyl for its part is optionally mono- or polysubstituted identically or differently by hydroxyl, —CO—O(C₁–C₄)-alkyl, —NH—CO—O(C₁–C₄)-alkyl, imidazolyl and/or hydroxyphenyl, R⁴ and R⁵ represent methyl, fluorine or chlorine or in particular hydrogen, R⁶ represents hydrogen, hydroxyl, OR¹⁰, NR¹¹R¹², methyl, ethyl, n-propyl, isopropyl n-, i-, s- or t-butyl, n-pentyl, (C₃–C₆)-cycloalkyl, (C₆–C₁₀)-aryl, or represents a saturated, unsaturated or aromatic 5- to 10-membered heterocycle having up to three identical or different heteroatoms from the series S, O and/or N, where the abovementioned hydrocarbon radicals and heterocycles are optionally substituted by one, two or three identical or different substituents from the group halogen, hydroxyl, cyano, nitro, amino, CF₃, (C₁–C₄)-alkyl, (C₁–C₄)-alkoxy, (C₃–C₈)-cycloalkyl, O—CO—R¹³, —CO—O—R¹⁴, —CO—NR¹⁵R¹⁶ or —NHCOOR¹⁷, where R¹⁰, R¹¹, R¹², R¹³, R¹⁴, R¹⁵, R¹⁶ and R¹⁷ are identical or different and each represent hydrogen, benzyl, (C₁–C₄)-alkyl or (C₃–C₆)-cycloalkyl, which for their part are optionally substituted by amino or (C₁–C₄)-alkoxy, or represents the radical

in which

R²⁰ and R²¹ together represent oxygen, or are each identical or different and represent hydrogen, halogen, hydroxyl, (C₁–C₄)-alkyl, (C₁–C₄)-alkoxy or the radical —NR¹⁵R¹⁶ and R²² represents hydrogen, hydroxyl, OR¹⁰, NR¹¹R¹², (C₁–C₄)-alkyl, (C₃–C₆)-cycloalkyl, (C₆–C₁₀)-aryl, or a saturated, unsaturated or aromatic 5- to 10-membered heterocycle having up to three identical or different heteroatoms from the series S, O and/or N, where the abovementioned hydrocarbon radicals and heterocycles are optionally substituted by one, two or three identical or different substituents from the group halogen, hydroxyl, cyano, nitro, amino, CF₃, (C₁–C₄)-alkyl, (C₁–C₄)-alkoxy, (C₃–C₈)-cycloalkyl, O—CO—R¹³, —CO—O—R¹⁴, —CO—NR¹⁵R¹⁶ or —NHCOOR¹⁷, where R¹⁰, R¹¹, R¹², R¹³, R¹⁴, R¹⁵, R¹⁶ and R¹⁷ are identical or different and each represent hydrogen, benzyl, (C₁–C₄)-alkyl or (C₃–C₆)-cycloalkyl, which for their part are optionally substituted by amino or (C₁–C₄)-alkoxy, R⁷ represents hydrogen, and their salts.

Particularly preferred compounds of the formula (I) are those in which Z is oxygen.

Particularly preferred compounds of the formula (I) are those in which R³ is the group —NH—CO—CO—R⁸ or —O—CH₂—CO—R⁸ and R⁸ is a group which in the sense of a prodrug can be broken down to the carboxylic acid or its salts. Particularly preferred compounds of the formula (I) are those in which R⁴, R⁵ and R⁷ represent hydrogen.

Particularly preferred compounds of the formula (I) are those in which R¹ and R² are both located in the ortho position relative to Z and represent bromine, trifluoromethyl, cyclopropyl and in particular methyl.

The compounds of the general formula (I) according to the invention can be prepared by reacting reactive indazole derivatives of the general formula (II) with reactive phenyl derivatives of the general formula (III)

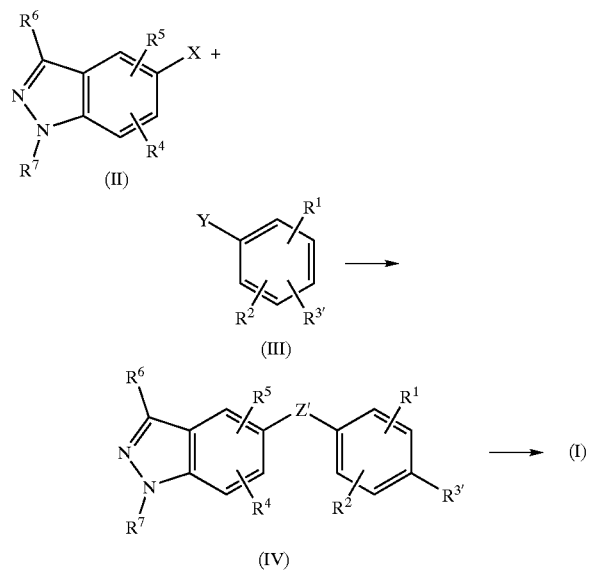

where the substituents R¹, R², R⁴, R⁵, R⁶ and R⁷ have the meaning indicated above and R³' has the meaning indicated for R³ or represents NO₂ or NPG, where PG is a protective group, X and Y each represent groups of opposite reactivity, where, for example, X can be an electrophilic radical which reacts with a nucleophilic Y substituent and vice versa, Z' has the meaning indicated for Z or represents

if appropriate in the presence of inert solvents and catalysts and if appropriate with isolation of the intermediates of the general formula (IV), or directly to give compounds of the formula (I).

Catalysts which may be mentioned by way of example are coupling catalysts such as Pd and/or Cu compounds.

The following may be mentioned by way of example for the reactive groups X and Y: halogen, hydroxyl, CH$_2$Br, mercapto, CHO, Li, MgHal, Sn or boron derivatives.

The indazoles of the general formula (II) employable according to the invention are known or can be prepared according to known methods (compare, for example, Ainsworth et al., J. Amer. Chem. Soc., 80, 1958, 965; Ainsworth et al., J. Amer. Chem. Soc., 79, 1957, 5245; Piozzi, F. et al., Gazz. Chim. Ital., 93 1963, 3–14; Simon, U, et al., Justus Liebigs Ann. Chem. 697, 1966, 17–41).

The phenyl derivatives of the general formula (III) are likewise known or can be prepared according to known methods (compare, for example, EP 580 550 A).

The reaction of the starting compounds (II) with (III) in general proceeds at normal pressure. However, it can also be carried out at elevated or reduced pressure.

The reaction can be carried out in a temperature range from −100° C. to 200° C., preferably between from −78° C. and 150° C., in the presence of inert solvents. Inert solvents which may preferably be mentioned are: dimethyl sulphoxide (DMSO), dimethylformamide (DMF), tetrahydrofuran (THF), diethyl ether etc.

Depending on the specific substituent pattern, in the reaction of (II) and (III) intermediates of the formula (IV) or (IV') can also result, in which, for example, the substituent R$^3$ represents a nitro group or Z represents a CHOH group, which can then be reduced to the corresponding amino groups or methylene groups according to customary methods with or without isolation of these intermediates and subsequently reacted further according to customary methods with carboxylic acids or carboxylic acid derivatives such as esters, anhydrides or halides to give amide compounds of the formula (I).

The process according to the invention can be illustrated by way of example by the following reaction schemes:

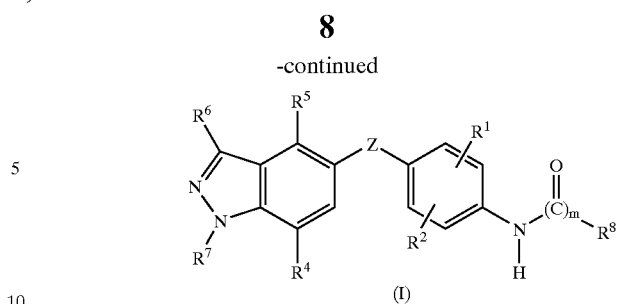

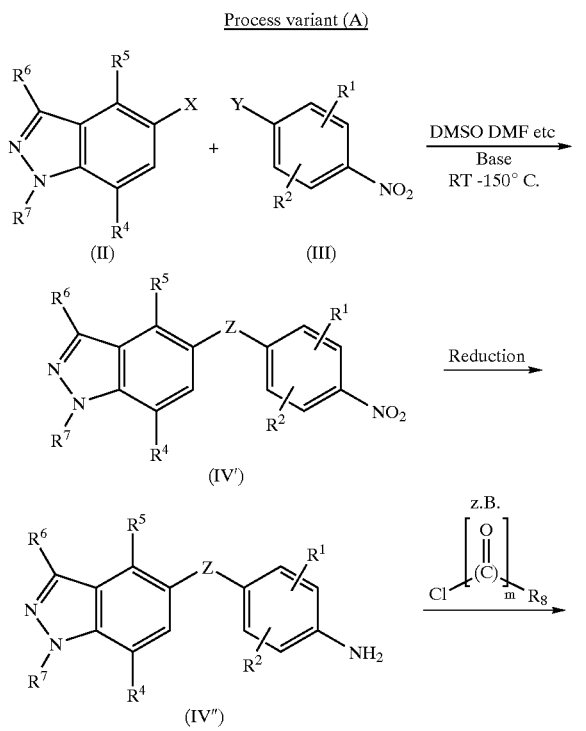

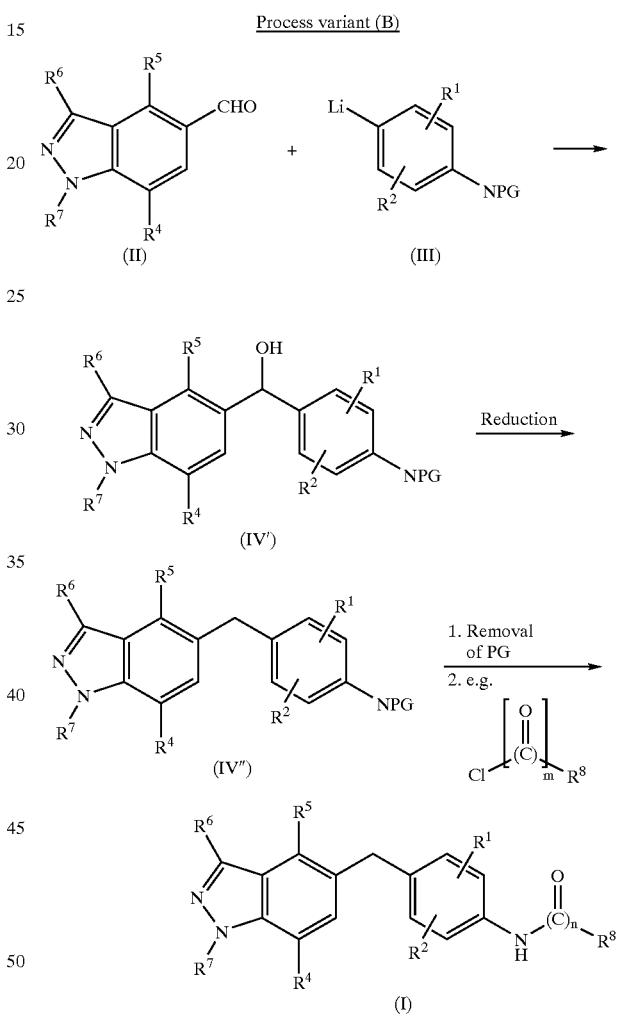

Depending on the meaning of the substituents R$^1$, R$^2$, R$^4$, R$^5$, R$^6$, R$^7$, it may be useful or necessary to vary these in individual process steps within the scope of meaning indicated.

The precursors and intermediates of the formula (IV) occurring in the reaction of (II) and (III) which are marked in the above reaction scheme by (IV') and (IV") are new. This application therefore also relates to compounds of the general formula (IV)

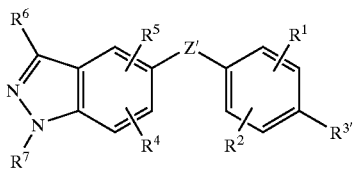

(IV)

in which

R¹, R², R⁴, R⁵, R⁶ and R⁷ have the meaning indicated above for formula (I),

Z' has the meaning indicated for Z or represents CHOH, and

R³' has the meaning indicated for R³ or represents NO₂ or NPG, where PG represents a protective group.

Protective groups (PG) are understood in the present application as meaning those groups in starting materials, intermediates and/or final products which protect functional groups present, such as carboxyl, amino or hydroxyl groups, and which are customary in preparative organic chemistry. The groups protected in this way can then be converted into free functional groups under known conditions in a simple manner.

The compounds of the formula (I) according to the invention show a surprising and valuable pharmacological spectrum of action and can therefore be employed as versatile medicaments. In particular, they can be employed in all indications which can be treated using natural thyroid hormones, such as, by way of example and preferably, depression, goitre or thyroid cancer. Arteriosclerosis, hypercholesterolaemia and dyslipidaemia can preferably be treated using the compounds of the formula (I) according to the invention. Adiposity and obesity and cardiac insufficiency can moreover also be treated and a postprandial lowering of the triglycerides achieved.

The compounds are also suitable for the treatment of certain respiratory tract disorders, namely in particular of pulmonary emphysema and for medicinally promoting maturation of the lungs.

The compounds are furthermore suitable for the treatment of pain and migraine, for neuronal repair (remyelinization) and for the treatment of Alzheimer's disease.

The compounds are furthermore suitable for the treatment of osteoporosis, cardiac arrhythmias, hypothyroidism and skin disorders.

Moreover, the compounds can also be employed for promotion and regeneration of hair growth and for the treatment of diabetes.

The active compounds according to the invention open up a further treatment alternative and are an enrichment of pharmacy. In comparison with the known and previously employed thyroid hormone preparations, the compounds according to the invention show an improved spectrum of action. They are preferably distinguished by great specificity, good tolerability and lower side effects, in particular in the cardiovascular area.

The efficacy of the compounds according to the invention can be tested, for example, in vitro by the T3 promoter assay cell test described below:

The test is carried out using a stably transfected, human HepG2 hepatocarcinoma cell which expresses a luciferase gene under the control of a thyroid hormone-regulated promoter. The vector used for the transfection carries a minimal thymidine kinase promoter ahead of the luciferase gene having a thyroid hormone-responsive element (TRE) which consists of two inverted palindromes of 12 bp each and one 8 bp spacer.

For the test, the cell cultures are inoculated into 96 well plates in Eagle's Minimal Essential Medium with the following additives: glutamine, tricine [N-(tris-(hydroxymethyl)-methyl)-glycine], sodium pyruvate, non-essential amino acids (L-Ala, L-Asn, L-Asp, L-Pro, L-Ser, L-Glu, Gly), insulin, selenium and transferrin. The cultures are grown at 37° C. and under a 10% $CO_2$ atmosphere for 48 hours. Serial dilutions of test substance or reference compound (T3, T4) and costimulator retinolic acid are then added to the test cultures and these are incubated for a further 48 or 72 hours as beforehand. Each substance concentration is tested in four replicates. For the determination of the luciferase induced by T3 or other substances, the cells are then lysed by addition of a Triton- and luciferase-containing buffer (Promega) and immediately measured luminometrically. The $EC_{50}$ values of each compound are calculated. Representative results for the compounds according to the invention are shown in Table 1:

TABLE 1

| Example | $EC_{50}$ [nM] |
| --- | --- |
| 4 | 115 |
| 9 | 190 |
| 11 | 10 |
| 11a | 13 |
| 16 | 10 |
| 18 | 18 |

The compounds according to the invention also surprisingly show advantageous properties in the tests described below:

Description of tests for finding pharmacologically active substances:

The substances which are to be investigated in vivo for their serum cholesterol-lowering action are administered orally to male mice having a body weight of between 25 and 35 g. The animals are divided into groups having an equal number of animals, as a rule n=7–10, one day before the start of the experiment. During the entire experiment, drinking water and feed are available to the animals ad libitum.

The substances are administered orally once daily for 7 days. For this purpose, the test substances are dissolved, for example, in a solution of Solutol HS 15+ethanol+saline solution (0.9%) in the ratio 1+1+8 or in a solution of Solutol HS 15+saline solution (0.9%) in the ratio 2+8. The dissolved substances are administered in a volume of 10 ml/kg of body weight using a stomach tube. The control group used is animals which have been treated exactly the same, but contain only the solvent (10 ml/kg of body weight) without test substance.

Before the first administration of substance, blood is taken from each mouse by puncture of the retroorbital venous plexus for the determination of the serum cholesterol (preliminary value). The test substance is then administered to the animals for the first time using a stomach tube. 24 hours after the last administration of substance (on the 8th day after the start of treatment), blood is again taken from each animal by puncture of the retroorbital venous plexus to determine the serum cholesterol. The blood samples are centrifuged and, after recovering the serum, the cholesterol is determined photometrically using an EPOS analyser 5050 (Eppendorf-Gerätebau, Netheler & Hinz GmbH, Hamburg). The determination is carried out using a commercially available enzyme test (Boehringer Mannheim, Mannheim).

The action of the test substances on the serum cholesterol concentration is determined by subtraction of the cholesterol value of the 1st blood sample (preliminary value) from the cholesterol value of the 2nd blood sample (after treatment). The differences of all cholesterol values of a group are averaged and compared with the average value of the differences of the control group.

Statistical analysis is carried out using Student's t test after prior testing of the variances for homogeneity.

Substances which statistically significantly ($p<0.05$) lower the serum cholesterol of the treated animals by at least 10% compared with that of the control group are regarded as pharmacologically active.

At the end of the experiment, the animals are weighed and sacrificed after taking blood. To check for potential cardiovascular side effects under the action of substance, the hearts are removed and weighed. An effect on the cardiovascular system can be determined by means of a significant increase in the heart weight. A further parameter which can be used for the substance action is a change in body weight.

In an analogous manner, for example, NMRI mice, ob,ob mice, Wistar rats or fa,fa diabetic rats can be used as experimental animals for this test.

A further in vivo test in which the compounds according to the invention surprisingly show advantageous properties is the cholesterol-fed rat animal model [A. Taylor et al., Molecular Pharmacology 52, 542–547 (1997); Z. Stephan et al., Atherosclerosis 126, 53–63 (1996)].

Furthermore, the cholesterol-lowering action of the compounds according to the invention can also be tested on normocholesterolaemic dogs by oral administration of the test substances for 5 to 7 days.

For the further investigation of potential cardiovascular side effects under the action of substance, inter alia the determination of the expression of the mRNA of the "HCN2" ion channel ("hyperpolarization-activated cyclic nucleotide-gated channel") in mouse or rat hearts can be used [cf. also: Trost et al., Endocrinology 141 (9), 3057–3064 (2000); Gloss et al., Endocrinology 142 (2), 544–550 (2001); Pachuki et al., Circulation Research 85, 498–503 (1999)]:

HCN2 Assay:

The quantification of the mRNa of the hyperpolarization-activated cyclic nucleotide-gated cation channel (HCN2) in rat hearts was carried out by means of real-time PCR (TaqMan PCR; Heid et al., Genome Res. 6 (10), 986–994). To this end, after preparation of the hearts the total RNA is isolated by means of RNaesy columns (Qiagen), digested with DNase and then transcribed into cDNA (SUPERSCRIPT II RT cDNA synthesis kit, from Gibco). The HCN2 mRNA determination is carried out on an ABI Prism 7700 apparatus (from Applied Biosystems). The sequence of the forward and reverse primers read: 5'-GGGAATCGACTCCGAGGTC-3' or 5'-GATCTTGGTGAAACGCACGA-3', that of the fluorescent sample 5'-6FAM-ACAAGACGGCCCGTGCACTACGC-TAMRA-3 (FAM= fluorescent dye 6-carboxyfluorescein; TAMRA=quencher 6-carboxytetramethylrhodamine). During the polymerase chain reaction, the fluorescent dye FAM is removed by means of the 5'-exonuclease activity of the taq polymerase and the previously quenched fluorescence signal is thereby obtained. The "threshold cycle" (Ct value) recorded is the number of cycles at which the fluorescence intensity was 10 standard deviations above the background fluorescence. The relative expression of the HCN2 mRNA calculated hereby is then standardized to the expression of the ribosomal protein L32.

In an analogous manner, this assay can also be carried out using mice hearts. The sequence of the forward and reverse primer in this case read 5'-CGAGGTGCTGGAGGAATACC-3' or 5'-CTAGCCGGTCAATAGCCACAG-3', that of the fluorescent sample 5'-6FAM-CATGATGCGGCGTGCCTTTGAG-TAMRA-3.

All customary administration forms are suitable for the administration of the compounds of the general formula (I), i.e. oral, parenteral, inhalant, nasal, sublingual, buccal, rectal or external, e.g. transdermal, in particular preferably oral or parenteral. In the case of parenteral administration, intravenous, intramuscular or subcutaneous administration may be mentioned in particular, e.g. as a subcutaneous depot. Oral administration is very particularly preferred.

In this case, the active compounds can be administered on their own or in the form of preparations. Suitable preparations for oral administration are, inter alia, tablets, capsules, pellets, coated tablets, pills, granules, solid and liquid aerosols, syrups, emulsions, suspensions and solutions. In this case, the active compound must be present in such an amount that a therapeutic action is achieved. In general, the active compound can be present in a concentration of 0.1 to 100% by weight, in particular 0.5 to 90% by weight, preferably 5 to 80% by weight. In particular, the concentration of the active compound should be 0.5 to 90% by weight, i.e. the active compound should be present in amounts which are sufficient to achieve the dosage range indicated.

For this purpose, the active compounds can be converted into the customary preparations in a known manner. This is carried out using inert, non-toxic, pharmaceutically suitable carriers, excipients, solvents, vehicles, emulsifiers and/or dispersants.

Excipients which may be mentioned by way of example are: water, non-toxic organic solvents such as paraffins, vegetable oils (e.g. sesame oil), alcohols (e.g. ethanol, glycerol), glycols (e.g. polyethylene glycol), solid carriers such as natural or synthetic ground minerals (e.g. talc or silicates), sugars (e.g. lactose), emulsifiers, dispersants (e.g. polyvinylpyrrolidone) and lubricants (e.g. magnesium sulphate).

In the case of oral administration, tablets, of course, can also contain additives such as sodium citrate together with additional substances such as starch, gelatin and the like. Aqueous preparations for oral administration can furthermore be mixed with flavour enhancers or colourants.

In the case of oral administration, doses of 0.001 to 5 mg/kg, preferably 0.005 to 3 mg/kg, of body weight are preferably administered every 24 hours.

The new active compounds can be administered on their own and, if required, also in combination with other active compounds, preferably from the group consisting of CETP inhibitors, antidiabetics, antioxidants, cytostatics, calcium antagonists, blood pressure-lowering agents, thyroid hormones, inhibitors of HMG-CoA reductase, inhibitors of HMG-CoA reductase gene expression, squalene synthesis inhibitors, ACAT inhibitors, circulation-promoting agents, platelet aggregation inhibitors, anticoagulants, angiotensin II receptor antagonists, cholesterol absorption inhibitors, MTP inhibitors, aldose reductase inhibitors, fibrates, niacin and PPAR agonists.

The following working examples are intended to illustrate the invention by way of example without restrictive action on the range of protection.

13
Starting Compounds

EXAMPLE I

5-Benzyloxy-2-nitrobenzaldehyde

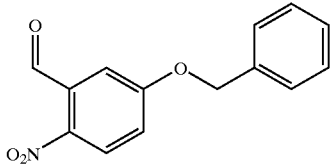

8.51 g (61.57 mmol) of potassium carbonate are added to a solution of 10.0 g (58.64 mmol) of 4-hydroxy-2-nitrobenzaldehyde in 70 ml of DMF. The solution is briefly stirred, then 10.53 g (61.57 mmol) of benzyl bromide are added and the reaction mixture is stirred at room temperature for 3 h. The resulting solid is then filtered off, 250 ml of water are added to the filtrate and the aqueous phase is extracted 3× with ethyl acetate. The organic phase is washed twice with water, dried over sodium sulphate, concentrated in vacuo and the residue is dried. 15.0 g (99%) of 4-benzyloxy-2-nitrobenzaldehyde are obtained as a yellow solid.

200 MHz $^1$H-NMR (DMSO): 5.33, s, 2H; 7.33–7.52, m, 7H; 8.20, d, 1H; 10.29, s, 1H.

EXAMPLE II

1-[5-(Benzyloxy)-2-nitrophenyl]-2-methyl-2-propen-1-ol

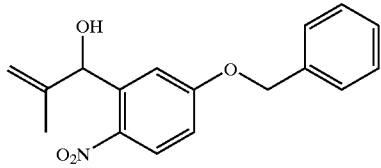

35.9 ml (16.33 mmol) of a 0.5 M isopropenylmagnesium bromide solution in THF are slowly added at −78° C. to a solution of 3.0 g (11.66 mmol) of 5-benzyloxy-2-nitrobenzaldehyde in 50 ml of THF. After addition is complete, the mixture is stirred at −78° C. for 2 h, then treated with 40 ml of water and warmed to room temperature. The mixture is treated with 10 ml of 1 N hydrochloric acid, the aqueous phase is extracted 2× with ethyl acetate, and the combined organic extracts are dried over sodium sulphate and freed from the solvent in vacuo. Purification of the crude product on silica gel ($CH_2Cl_2$) affords 1.7 g (48.7%) of 1-[5-(benzyloxy)-2-nitrophenyl]-2-methyl-2-propen-1-ol as a yellow oil.

200 MHz $^1$H-NMR (DMSO): 1.62, s, 3H; 4.66, m, 1H; 4.78, m, 1H; 5.74, s, 2H; 5.68, d, 1H; 5.85, d, 1H; 7.12, dd, 1H; 7.30–7.51, m, 6H; 8.00, d, 1H.

14
EXAMPLE III

1-[5-(Benzyloxy)-2-nitrophenyl]-3-methyl-2-buten-1-ol

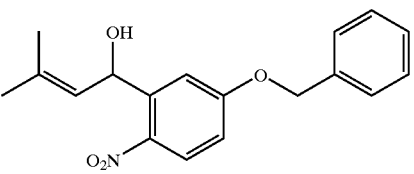

In an analogous manner to the procedure of Example II, 2.88 g (11.20 mmol) of 5-benzyloxy-2-nitrobenzaldehyde in 30 ml of THF are reacted at −78° C. with 31.7 ml (15.67 mmol) of a 0.5 M 2-methyl-propenylmagnesium bromide soln in THF to give 1.8 g (51%) of 1-[5-(benzyloxy)-2-nitrophenyl]-3-methyl-2-buten-1-ol.

300 MHz $^1$H-NMR (DMSO): 1.65, s, 3H; 1.72, s, 3H; 5.10, d, 1H; 5.23, s, 2H; 5.50, d, 1H; 5.87, dd, 1H; 7.08, dd, 1H; 7.32–7.50, m, 6H; 7.89, d, 1H.

EXAMPLE IV

1-[5-(Benzyloxy)-2-nitrophenyl]-2-hexin-1-ol

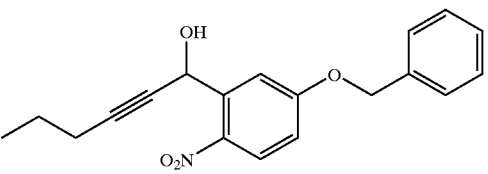

Analogously to the procedure of Example II, starting from 3.173 g (12.34 mmol) of 5-benzyloxy-2-nitrobenzaldehyde in 30 ml of THF and a 1-pentinylmagnesium bromide soln at −78° C. obtained from 2.5 g (36.70 mmol) of 1-pentine and 10.6 ml (31.93 mmol) of 3 M ethylmagnesium bromide soln in diethyl ether at 0° C., 1.82 g (45%) of 1-[5-(benzyloxy)-2-nitrophenyl]-2-hexin-1-ol are obtained.

200 MHz $^1$H-NMR (DMSO): 0.88, t, 3H; 1.40, m, 2H; 2.14, dt, 2H; 5.26, s, 2H; 5.97, dt, 1H; 6.29, d, 1H; 7.14, dd, 1H; 7.32–7.52, m, 6H; 8.02, d, 1H.

EXAMPLE V

E/Z-1-[5-(Benzyloxy)-2-nitrophenyl]-2-buten-1-ol

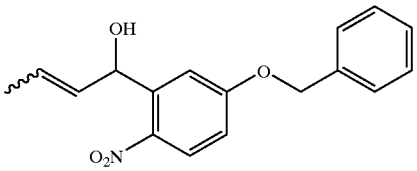

Analogously to the procedure of example II, starting from 3.00 g (11.66 mmol) of 5-benzyloxy-2-nitrobenzaldehyde in 60 ml of THF and 37.8 ml (18.66 mmol) of a 0.5 M 1-propenylmagnesium bromide solution in THF at −78° C., 1.95 g (56%) of 1-[5-(benzyloxy)-2-nitrophenyl]-2-buten-1-ol are obtained as an E/Z mixture.

300 MHz $^1$H-NMR (DMSO): 1.70 (1.60), dd, 3H; 5.22, s, 2H; 5.35 (5.53), m, 1H; 5.60, m, 1H; 5.66 (5.65), d, 1H; 5.97 (5.66), dd, 1H; 7.09, dd, 1H; 7.31–7.50, m, 6H; 7.92 (7.95), d, 1H.

EXAMPLE VI

1-[5-(Benzyloxy)-2-nitrophenyl]-2-methyl-2-propen-1-one

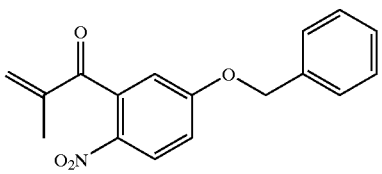

3.67 g (42.23 mmol) of manganese dioxide are suspended in a solution of 1.58 g (5.28 mmol) of 1-[5-(benzyloxy)-2-nitrophenyl]-2-methyl-2-propen-1-ol in 30 ml of dichloromethane. The suspension is heated under reflux overnight, and after cooling to room temperature the mixture is filtered through kieselguhr, the residue is washed with dichloromethane and the filtrate is concentrated in vacuo and dried. 1.34 g (85%) of 1-[5-(benzyloxy)-2-nitrophenyl]-2-methyl-2-propen-1-one are obtained.

300 MHz $^1$H-NMR (DMSO): 1.97, s, 3H; 5.29, s, 2H; 5.39, s, 1H; 5.97, s, 1H; 7.16, d, 1H; 7.30–7.50, m, 6H; 8.22, d, 1H.

EXAMPLE VII

1-[5-(Benzyloxy)-2-nitrophenyl]-3-methyl-2-buten-1-one

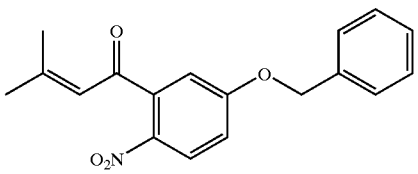

In an analogous manner to the procedure of Example VI, 1.70 g (5.43 mmol) of 1-[5-(benzyloxy)-2-nitrophenyl]-3-methyl-2-buten-1-ol are reacted with 4.25 g (48.83 mmol) of manganese dioxide in 30 ml of dichloromethane to give 1.37 g (81%) of 1-[5-(benzyloxy)-2-nitrophenyl]-3-methyl-2-buten-1-one.

400 MHz $^1$H-NMR (DMSO): 1.94, s, 3H; 2.10, s, 3H; 5.29, s, 2H; 6.32, s, 1H; 7.13, d, 1H; 7.27, dd, 1H; 7.32–7.50, m, 5H; 8.12, d, 1H.

EXAMPLE VIII

1-[5-(Benzyloxy)-2-nitrophenyl]-2-hexin-1-one

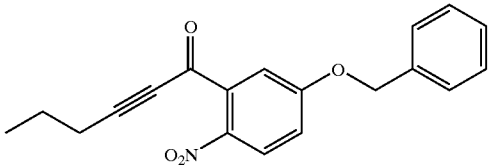

Analogously to the procedure of Example VI, starting from 1.77 g (5.44 mmol) of 1-[5-(benzyloxy)-2-nitrophenyl]-2-hexin-1-ol and 4.26 g (48.96 mmol) of manganese dioxide in 30 ml of dichloromethane, 1.46 g (83%) of 1-[5-(benzyloxy)-2-nitrophenyl]-2-hexin-1-one are obtained.

300 MHz $^1$H-NMR (DMSO): 0.92, t, 3H; 1.52, sext., 2H; 2.48, t, 2H; 5.30, s, 2H; 7.33–7.50, m, 7H; 8.11, d, 1H.

EXAMPLE IX

E/Z-1-[5-(Benzyloxy)-2-nitrophenyl]-2-buten-1-one

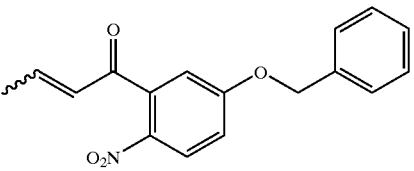

Analogously to the procedure of Example VI, starting from 1.94 g (6.50 mmol) of E/Z-1-[5-(benzyloxy)-2-nitrophenyl]-2-buten-1-ol and 5.08 g (58.45 mmol) of manganese dioxide in 25 ml of dichloromethane, 1.31 g (68%) of E/Z-1-[5-(benzyloxy)-2-nitrophenyl]-2-buten-1-one are obtained.

200 MHz $^1$H-NMR (DMSO): 1.89 (2.00), d, 3H; 5.29, s, 2H; 6.42 (6.42), m, 2H; 7.10 (7.18), d, 1H; 7.30, dd, 1H; 7.35–7.51, m, 5H; 8.21 (8.17), d, 1H.

EXAMPLE X 1-(2-Amino-5-hydroxyphenyl)-2-methyl-1-propanone

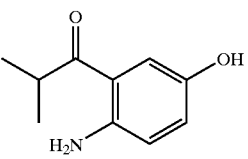

0.2 g of palladium/carbon (10%) is suspended in a solution of 1.34 g (4.51 mmol) of 1-[5-(benzyloxy)-2-nitrophenyl]-2-methyl-2-propen-1-one in 50 ml of ethanol. The mixture is shaken under a hydrogen atmosphere at 3 bar for 4.5 h, then the mixture is filtered off through kieselguhr, the filtrate is concentrated in vacuo and the residue is purified on silica gel (cyclohexane/ethyl acetate 5:2–1:1). 511 mg (63%) of 1-(2-amino-5-hydroxyphenyl)-2-methyl-1-propanone are obtained.

400 MHz $^1$H-NMR (DMSO): 1.08, d, 6H; 3.46, sept, 1H; 6.62, d, 1H; 6.64, s, 2H; 6.82, dd, 1H; 7.13, d, 1H; 8.61, s, 1H.

EXAMPLE XI 1-(2-Amino-5-hydroxyphenyl)-3-methyl-1-butanone

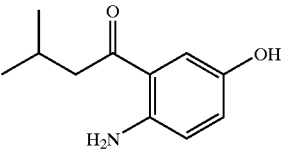

In an analogous manner to the procedure of Example X, 1.33 g (4.27 mmol) of 1-[5-(benzyloxy)-2-nitrophenyl]-3-methyl-2-buten-1-one are reacted with 0.20 g of palladium/carbon (10%) in 50 ml of ethanol under hydrogen in the course of 3 h to give 825 mg (100%) of 1-(2-amino-5-hydroxyphenyl)-3-methyl-11-butanone.

300 MHz $^1$H-NMR (DMSO): 0.92, d, 6H; 2.12, sept, 1H; 2.70, d, 2H; 6.60, s, broad, 2H; 6.62, d, 1H; 6.81, dd, 1H; 7.09, d, 1H; 8.60, s, broad, 1H.

EXAMPLE XII 1-(2-Amino-5-hydroxyphenyl)-1-hexanone

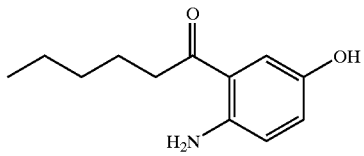

Analogously to the procedure of Example X, starting from 1.44 g (4.45 mmol) of 1-[5-(benzyloxy)-2-nitrophenyl]-2-hexin-1-one with 0.20 g of palladium/carbon (10%) in 50 ml of ethanol under hydrogen, after 3 h 874 mg (95%) of 1-(2-amino-5-hydroxyphenyl)-1-hexanone are obtained.

200 MHz $^1$H-NMR (DMSO): 0.88, t, 3H; 1.30, m, 4H; 1.57, quint., 2H; 2.81, t, 2H; 6.60, d, 1H; 6.63, s, broad, 2H; 6.81, dd, 1H; 7.10, d, 1H; 8.64, s, broad, 1H.

EXAMPLE XIII (2-Amino-5-hydroxy)phenyl-butanone

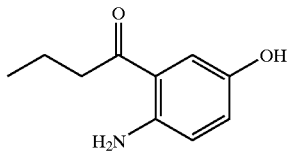

Analogously to the procedure of Example X, starting from 1.31 g (4.42 mmol) of E/Z-1-[5-(benzyloxy)-2-nitrophenyl]-2-buten-1-one with 0.17 g of palladium/carbon (10%) in 30 ml of ethanol under hydrogen, after 3 h 770 mg (97%) of 1-(2-amino-5-hydroxyphenyl)-1-butanone are obtained.

400 MHz $^1$H-NMR (DMSO): 0.92, t, 2H; 1.59, sext., 2H; 2.81, t, 2H; 6.61, s, broad, 2H; 6.62, d, 1H; 6.81, dd, 1H; 7.10, d, 1H; 8.62, s, broad, 1H.

EXAMPLE XIV

5-Hydroxy-3-isopropyl-1H-indazole

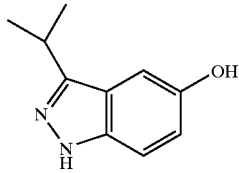

A solution of 900 mg (5.02 mmol) of 1-(2-amino-5-hydroxyphenyl)-2-methyl-1-propanone in 30 ml of half-conc. hydrochloric acid is treated slowly at −5° C. with a solution of 364 mg (5.27 mmol) of sodium nitrite in 15 ml of water and, after addition is complete, stirred at this temperature for 30 min. A solution of 2.266 g (10.04 mmol) of tin(II) chloride dihydrate in 15 ml of conc. hydrochloric acid is then added dropwise to the reaction mixture at −5° C. and the reaction is slowly warmed to room temperature. The mixture is neutralized using 45% strength sodium hydroxide solution, filtered off through kieselguhr, washed with ethyl acetate, and the organic phase is dried over sodium sulphate, concentrated in vacuo and dried. 370 mg (36%) of 5-hydroxy-3-isopropyl-1H-indazole are obtained.

300 MHz $^1$H-NMR (DMSO): 1.32, d, 6H; 3.23, sept., 1H; 6.85, dd, 1H; 6.95, d, 1H; 7.26, d, 1H; 8.93, s, broad, 1H; 12.23, s, broad, 1H.

EXAMPLE XV

5-Hydroxy-3-isobutyl-1H-indazole

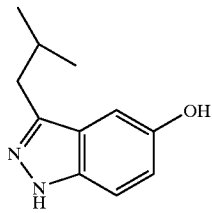

In an analogous manner to the procedure of Example XIV, 783 mg (4.05 mmol) of 1-(2-amino-5-hydroxyphenyl)-3-methyl-1-butanone in 30 ml of half-conc. hydrochloric acid are reacted with 294 mg (4.25 mmol) of sodium nitrite in 15 ml of water and 914 mg (4.05 mmol) of tin(II) chloride dihydrate in 15 ml of conc. hydrochloric acid to give 317 mg (41%) of 5-hydroxy-3-isobutyl-1H-indazole.

300 MHz $^1$H-NMR (DMSO): 0.91, d, 6H; 2.03, m, 1H; 2.67, d, 2H; 6.85, dd, 1H; 6.88, s, 1H; 7.26, d, 1H; 8.92, s, broad, 1H; 12.30, s, broad, 1H.

EXAMPLE XVI

5-Hydroxy-3-pentyl-1H-indazole

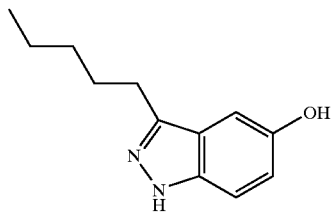

Analogously to the procedure of Example XIV, starting from 943 mg (4.55 mmol) of 1-(2-amino-5-hydroxyphenyl)-1-hexanone in 30 ml of half-conc. hydrochloric acid with 330 mg (4.78 mmol) of sodium nitrite in 15 ml of water and 1.027 g (4.55 mmol) of tin(II) chloride dihydrate in 15 ml of conc. hydrochloric acid, 254 mg (27%) of 5-hydroxy-3-pentyl-1H-indazole are obtained.

400 MHz $^1$H-NMR (DMSO): 0.87, t, 3H; 1.32, m, 4H; 1.69, m, 2H; 2.78, t, 2H; 6.85, dd, 1H; 6.89, d, 1H; 7.26, d, 1H; 8.94, s, broad, 1H; 12.27, s, broad, 1H.

EXAMPLE XVII

5-Hydroxy-3-propyl-1H-indazole

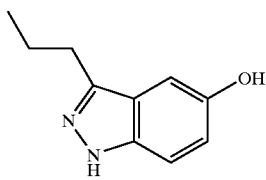

Analogously to the procedure of Example XIV, starting from 730 mg (4.07 mmol) of 1-(2-amino-5-hydroxyphenyl)-1-butanone in 20 ml of half-conc. hydrochloric acid with 295 mg, (4.28 mmol) of sodium nitrite in 15 ml of water and 919 mg (4.07 mmol) of tin(II) chloride dihydrate in 15 ml conc. hydrochloric acid, 180 mg (25%) of 5-hydroxy-3-propyl-1H-indazole are obtained.

200 MHz $^1$H-NMR (DMSO): 0.92, t, 3H; 1.71, sext., 2H; 2.77, t, 2H; 6.85, dd, 1H; 6.88, d, 1H; 7.27, d, 1H; 8.97, s, broad, 1H; 12.30, s, broad, 1H.

EXAMPLE XVIII

5-(2,6-Dimethyl-4-nitrophenoxy)-3-isopropyl-1H-indazole

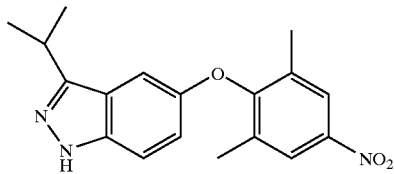

86 mg (0.624 mmol) of potassium carbonate are added to a solution of 110 mg (0.624 mmol) of 5-hydroxy-3-isopropyl-1H-indazole in 5 ml of DMSO and the mixture is stirred for 1 h. After addition of 106 mg (0.624 mmol) of 4-fluoro-3,5-dimethylnitrobenzene in portions, the mixture is then firstly stirred at room temperature for 2 h, then at 100° C. for 3 h. After cooling to room temperature, the mixture is added to 10 ml of water and the aqueous phase is extracted 3× with ethyl acetate. The combined organic extracts are washed with water and satd NaCl soln, dried over sodium sulphate and concentrated in vacuo. By purification of the resulting residue on silica gel (cyclohexane/ethyl acetate 3:1), 84 mg (41%) of 5-(2,6-dimethyl-4-nitrophenoxy)-3-isopropyl-1H-indazole are obtained.

200 MHz $^1$H-NMR (DMSO): 1.26, d, 6H; 2.19, s, 6H; 3.22, sept., 1H; 6.89, d, 1H; 6.98, dd, 1H; 7.46, d, 1H; 8.13, s, 2H; 12.58, s, broad, 1H.

EXAMPLE XIX

5-(2,6-Dimethyl-4-nitrophenoxy)-3-isobutyl-1H-indazole

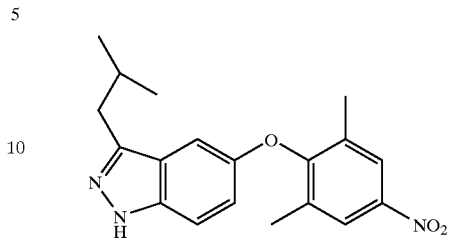

In an analogous manner to the procedure of Example XVIII, 136 mg (0.715 mmol) of 5-hydroxy-3-isobutyl-1H-indazole are reacted with 99 mg (0.715 mmol) of potassium carbonate and 121 mg (0.715 mmol) of 4-fluoro-3,5-dimethylnitrobenzene in 5 ml of DMSO to give 92 mg (38%) of 5-(2,6-dimethyl-4-nitrophenoxy)-3-isobutyl-1H-indazole.

200 MHz $^1$H-NMR (DMSO): 0.85, d, 6H; 1.96, sept, 1H; 2.18, s, 6H; 2.66, d, 2H; 6.85, d, 1H; 7.00, dd, 1H; 7.46, d, 1H; 8.13, s, 2H; 12.65, s, broad, 1H.

EXAMPLE XX

5-(2,6-Dimethyl-4-nitrophenoxy)-3-pentyl-1H-indazole

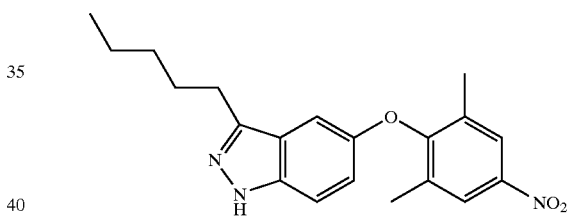

Analogously to the procedure of Example XVIII, starting from 246 mg (1.204 mmol) of 5-hydroxy-3-pentyl-1H-indazole, 166 mg (1.204 mmol) of potassium carbonate and 204 mg (1.204 mmol) of 4-fluoro-3,5-dimethylnitrobenzene in 5 ml of DMSO, 200 mg (47%) of 5-(2,6-dimethyl-4-nitrophenoxy)-3-pentyl-1H-indazole are obtained.

200 MHz $^1$H-NMR (DMSO): 0.79, t, 3H; 1.23, m, 4H; 1.61, m, 2H; 2.19, s, 6H; 2.75, t, 2H; 6.81, d, 1H; 7.03, dd, 1H; 7.46, d, 1H; 8.12, s, 2H; 12.62, s, broad, 1H.

EXAMPLE XXI

5-(2,6-Dimethyl-4-nitrophenoxy)-3-propyl-1H-indazole

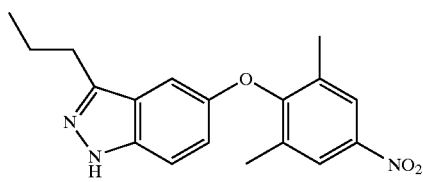

Analogously to the procedure of Example XVIII, starting from 150 mg (0.851 mmol) of 5-hydroxy-3-propyl-1H-indazole with 118 mg (0.851 mmol) of potassium carbonate and 144 mg (0.851 mmol) of 4-fluoro-3,5-dimethylnitrobenzene in 5 ml of DMSO, 209 mg (75%) of 5-(2,6-dimethyl-4-nitrophenoxy)-3-propyl-1H-indazole are obtained.

200 MHz $^1$H-NMR (DMSO): 0.89, t, 3H; 1.65, sext., 2H; 2.19, s, 6H; 2.74, t, 2H; 6.85, d, 1H; 7.01, dd, 1H; 7.46, d, 1H; 8.16, s, 2H; 12.63, s, broad, 1H.

EXAMPLE XXII 1-tert-Butoxycarbonyl-5-(4-amino-2,6-dimethylphenoxy)-3-pentylindazole

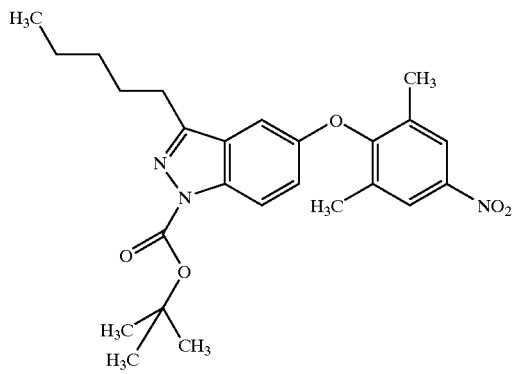

889 mg (4.074 mmol) of tert-butyl pyrocarbonate are added at 0° C. to a suspension of 1.20 g (3.395 mmol) of 5(2,6-dimethyl-4-nitrophenoxy)-3-pentyl-1H-indazole (Example XX), 378 mg (3.735 mmol) of triethylamine and 41 mg (0.340 mmol) of 4-dimethylaminopyridine in 5 ml of tetrahydrofuran and 5 ml of acetonitrile and the mixture is stirred at room temperature for 30 min. The reaction mixture is then freed from the solvent in vacuo, taken up with ethyl acetate, and the organic phase is washed once each with 1N hydrochloric acid, satd sodium hydrogencarbonate solution and satd. sodium chloride solution, dried over sodium sulphate, freed from the solvent in vacuo and purified on silica gel using methylene chloride. 1.57 g (92% of theory) of 1-tert-butoxycarbonyl-5-(2,6-dimethyl-4-nitrophenoxy)-3-pentyl-1H-indazole are obtained.

$^1$H NMR (300 MHz, DMSO-d$_6$): δ=0.81 (t, 3H), 1.25 (m, 4H), 1.62 (s, 9H), 1.63 (m, 2H), 2.19 (s, 6H), 2.82 (t, 2H), 7.09 (d, 1H), 7.18 (dd, 1H), 7.99 (d, 1H), 8.17 (s, 2H).

EXAMPLE XXIII 1-tert-Butoxycarbonyl-5-(4-amino-2,6-dimethylphenoxy)-3-pentylindazole

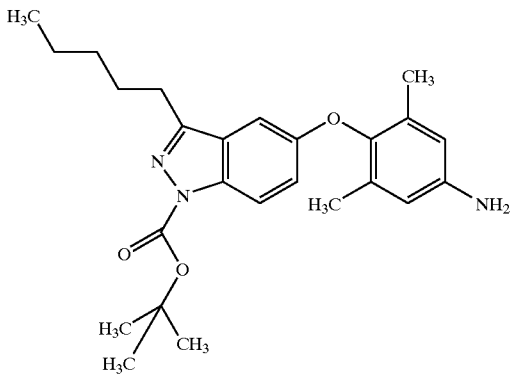

A suspension of 1.570 g (3.116 mmol) of 1-tert-butoxycarbonyl-5-(2,6-dimethyl-4-nitrophenoxy)-3-pentylindazole (Example XXII) and 250 mg (2.349 mmol) of palladium/carbon (10%) in 25 ml of ethanol are hydrogenated under a hydrogen atmosphere for 2 h. The reaction mixture is filtered off through kieselguhr, and the filtrate is concentrated in vacuo and dried. 1.385 g (95% or theory) of 1-tert-butoxycarbonyl-5-(4-amino-2,6-dimethylphenoxy)-3-pentyl-1H-indazole are obtained.

$^1$H NMR (300 MHz, DMSO-d$_6$): δ=0.83 (t, 3H), 1.27 (m, 4H), 1.62 (s, 9H), 1.66 (m, 2H), 1.92 (s, 6H), 2.29 (t, 2H), 4.95 (s, broad, 1H), 6.37 (s, 2H), 6.90 (d, 1H), 7.10 (dd, 1H), 7.95 (d, 1H).

PREPARATION EXAMPLES

EXAMPLE 1

5-(4-Amino-2,6-dimethylphenoxy)-3-isopropyl-1H-indazole

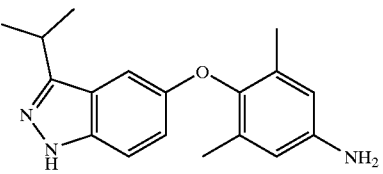

25 mg of palladium/carbon (10%) are suspended in a solution of 175 mg (0.538 mmol) of 5-(2,6-dimethyl-4-nitrophenoxy)-3-isopropyl-1H-indazole in 10 ml of ethanol. The mixture is shaken under a hydrogen atmosphere at 3 bar for 4 h, then filtered off through kieselguhr, the filtrate is concentrated in vacuo and the residue is purified on silica gel (cyclohexane/ethyl acetate 2:1). 50 mg (31%) of 5-(4-amino-2,6-dimethylphenoxy)-3-isopropyl-1H-indazole are obtained.

400 MHz $^1$H-NMR (DMSO): 1.26, d, 6H; 1.94, s, 6H; 3.16, sept., 1H; 4.81, s, broad, 2H; 6.33, s, 2H; 6.72, d, 1H; 6.94, dd, 1H; 7.38, d, 1H; 12.44, s, broad, 1H.

EXAMPLE 2

5-(4-Amino-2,6-dimethylphenoxy)-3-isobutyl-1H-indazole

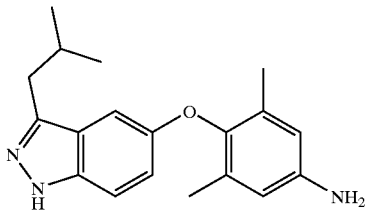

In an analogous manner to the procedure of Example 1, 172 mg (0.507 mmol) of 5-(2,6-dimethyl-4-nitrophenoxy)-3-isobutyl-1H-indazole are reacted with 25 mg of palladium/carbon (10%) in 15 ml of ethanol under hydrogen in the course of 3 h to give 100 mg (64%) of 5-(4-amino-2,6-dimethylphenoxy)-3-isobutyl-1H-indazole.

300 MHz $^1$H-NMR (DMSO): 0.86, d, 6H; 1.92, s, 6H; 1.95, m, 1H; 2.61, d, 2H; 4.80, s, broad, 2H; 6.34, s, 2H; 6.69, d, 1H; 6.96, dd, 1H; 7.38, d, 1H; 12.49, s, broad, 1H.

EXAMPLE 3 AND EXAMPLE 3a 5-(4-Amino-2,6-dimethylphenoxy)-3-pentyl-1H-indazole (Example 3) and 5-(4-ethylamino-2,6-dimethylphenoxy)-3-pentyl-1H-indazole (Example 3a)

(Example 3)

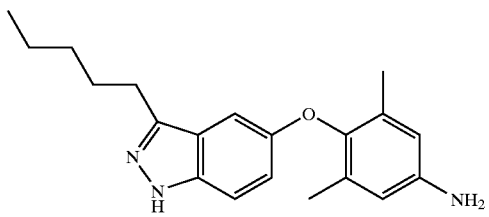

(Example 3a)

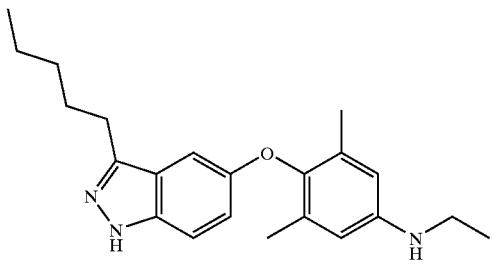

Analogously to the procedure of Example 1, starting from 181 mg (0.512 mmol) of 5-(2,6-dimethyl-4-nitrophenoxy)-3-pentyl-1H-indazole with 30 mg of palladium/carbon (10%) in 10 ml of ethanol under hydrogen, in the course of 20 h 92 mg (5%) of 5-(4-amino-2,6-dimethylphenoxy)-3-pentyl-1H-indazole (Example 3) and 20 mg (11%) of 5-(4-ethylamino-2,6-dimethylphenoxy)-3-pentyl-1H-indazole (Example 3a) are obtained.

EXAMPLE 3

200 MHz $^1$H-NMR (DMSO): 0.81, t, 3H; 1.24, m, 4H; 1.61, m, 2H; 1.91, s, 6H; 2.72, t, 2H; 4.84, s, broad, 2H; 6.33, s, 2H; 6.68, d, 1H; 6.97, dd, 1H; 7.38, d, 1H; 12.48, s, broad, 1H.

EXAMPLE 3a

200 MHz $^1$H-NMR (DMSO): 0.81, t, 3H; 1.18, t, 3H; 1.25, m, 4H; 1.61, m, 2H; 1.96, s, 6H; 2.72, t, 2H; 3.01, quint., 2H; 5.30, t, 1H; 6.31, s, 2H; 6.68, d, 1H; 6.97, dd, 1H; 7.39, d, 1H; 12.48, s, broad, 1H.

EXAMPLE 4

5-(4-Amino-2,6-dimethylphenoxy)-3-propyl-1H-indazole

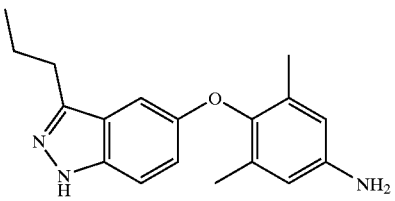

Analogously to the procedure of Example 1, starting from 243 mg (0.747 mmol) of 5-(2,6-dimethyl-4-nitrophenoxy)-3-propyl-1H-indazole with 30 mg of palladium/carbon (10%) in 10 ml of ethanol under hydrogen, in the course of 3 h 35 mg (16%) of 5-(4-amino-2,6-dimethylphenoxy)-3-propyl-1H-indazole are obtained.

200 MHz $^1$H-NMR (DMSO): 0.88, t, 3H; 1.63, sext., 2H; 1.92, s, 6H; 2.72, t, 2H; 4.82, s, broad, 2H; 6.34, s, 2H; 6.67, d, 1H; 6.96, dd, 1H; 7.38, d, 1H; 12.49, s, broad, 1H.

EXAMPLE 5

Ethyl [5-(4-{[ethoxy(oxo)acetyl]amino}-2,6-dimethylphenoxy)-3-isopropyl-1H-indazol-1-yl](oxo)acetate

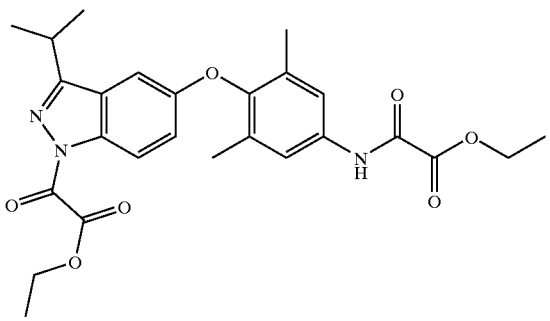

19.4 mg (0.142 mmol) of ethyl oxalyl chloride are added dropwise at 0° C. to a solution of 40 mg (0.135 mmol) of 5-(4-amino-2,6-dimethylphenoxy)-3-isopropyl-1H-indazole and 12.3 mg (0.122 mmol) of triethylamine in 8 ml of dichloromethane. The mixture is subsequently stirred at room temperature for 3 h and then treated with 10 ml of phosphate buffer. The organic phase is washed with 0.5 M hydrochloric acid, water, satd NaHCO$_3$ solution and water, dried over sodium sulphate and concentrated in vacuo. After purification of the residue on silica gel (cyclohexane/CH$_2$Cl$_2$ 1:2), 64 mg (90%) of ethyl [5-(4-{[ethoxy(oxo)acetyl]amino}-2,6-dimethylphenoxy)-3-isopropyl-1H-indazol-1-yl](oxo)acetate are obtained.

200 MHz $^1$H-NMR (DMSO): 1.20–1.40, m, 12H; 2.08, s, 6H; 3.30, m, 1H; 4.32, q, 2H; 4.47, q, 2H; 7.19, dd, 1H; 7.21, d, 1H; 7.58, s, 2H; 8.16, d, 1H; 10.76, s, broad, 1H.

EXAMPLE 6

Ethyl [5-(4-{[ethoxy(oxo)acetyl]amino}-2,6-dimethylphenoxy)-3-isobutyl-1H-indazol-1-yl](oxo)acetate

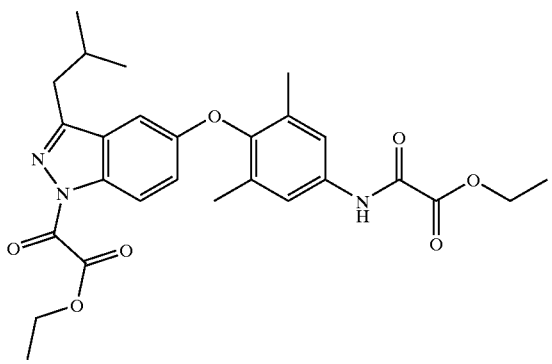

In an analogous manner to the procedure of Example 5, 82 mg (0.265 mmol) of 5-(4-amino-2,6-dimethylphenoxy)-3-isobutyl-1H-indazole, 36.2 mg (0.265 mmol) of triethylamine and 26.8 mg (0.265 mmol) of ethyl oxalyl chloride are reacted to give 56 mg (41%) of ethyl [5-(4-{[ethoxy(oxo)acetyl]amino}-2,6-dimethylphenoxy)-3-isobutyl-1H-indazol-1-yl](oxo)acetate.

200 MHz $^1$H-NMR (DMSO): 0.92, d, 6H; 1.33, t, 6H; 2.15, s, 6H; 2.19, m, 1H; 2.78, d, 2H; 4.33, q, 2H; 4.43, q, 2H; 7.19, d, 1H; 7.21, dd, 1H; 7.60, s, 2H; 8.16, d, 1H; 10.27, s, broad, 1H.

EXAMPLE 7

Ethyl [5-(4-{bis[ethoxy(oxo)acetyl]amino}-2,6-dimethylphenoxy)-3-pentyl-1H-indazol-1-yl](oxo)acetate

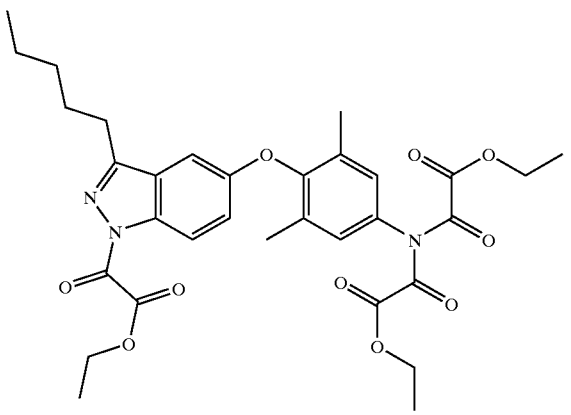

Analogously to the procedure of Example 5, starting from 67 mg (0.207 mmol) of 5-(4-amino-2,6-dimethylphenoxy)-3-pentyl-1H-indazole, 18.9 mg (0.186 mmol) of triethylamine and 28.3 mg (0.207 mmol) of ethyl oxalyl chloride, 100 mg (77%) of ethyl [5-(4-{bis[ethoxy(oxo)acetyl]amino}-2,6-dimethylphenoxy)-3-pentyl-1H-indazol-1-yl)(oxo)acetate are obtained.

200 MHz $^1$H-NMR (DMSO): 0.82, t, 3H; 1.19, t, 6H; 1.30, m, 4H; 1.34, t, 3H; 1.60, m, 2H; 2.11, s, 6H; 2.87, t, 2H; 4.29, q, 4H; 4.46, q, 2H; 7.10, d, 1H; 7.22, dd, 1H; 7.38, s, 2H; 8.20, d, 1H.

EXAMPLE 8 AND EXAMPLE 8a

Ethyl [5-(4-{[ethoxy(oxo)acetyl]amino}-2,6-dimethylphenoxy)-3-propyl-1H-indazol-1-yl](oxo)acetate (Example 8) and ethyl ({3,5-dimethyl-4-[(3-propyl-1H-indazol-5-yl)oxy]phenyl}amino)(oxo)acetate (Example 8a)

(Example 8)

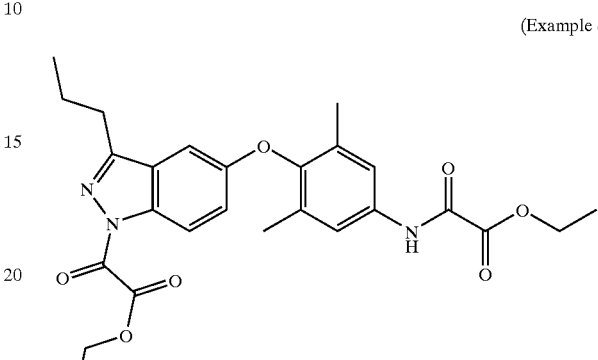

(Example 8a)

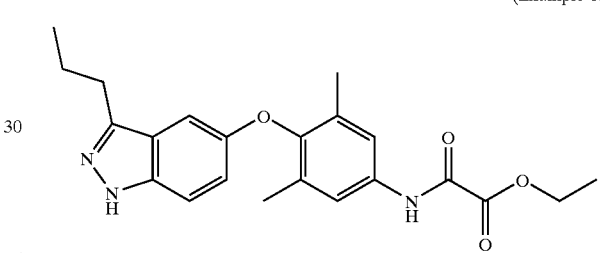

Analogously to the procedure of Example 5, starting from 34 mg (0.115 mmol) of 5-(4-amino-2,6-dimethylphenoxy)-3-propyl-1H-indazole, 11.6 mg (0.115 mmol) of triethylamine and 15.7 mg (0.115 mmol) of ethyl oxalyl chloride, 18 mg, (32%) of ethyl [5-(4-{[ethoxy(oxo)acetyl]amino}-2,6-dimethylphenoxy)-3-propyl-1H-indazol-1-yl](oxo)acetate (Example 8) are obtained. Moreover, 18 mg, (40%) of ethyl ({3,5-dimethyl-4-[(3-propyl-1H-indazol-5-yl)oxy]phenyl}amino)(oxo)acetate (Example 8a) are obtained.

EXAMPLE 8

200 MHz $^1$H-NMR (DMSO): 0.92, t, 3H; 1.33, t, 6H; 1.70, q, 2H; 2.07, s, 6H; 2.87, t, 2H; 4.32, q, 2H; 4.46, q, 2H; 7.19, d, 1H; 7.21, dd, 1H; 7.59, s, 2H; 8.17, d, 1H; 10.25, s, broad, 1H.

EXAMPLE 8a

200 MHz $^1$H-NMR (CDCl$_3$+DMSO): 0.96, t, 3H; 1.44, t, 3H; 1.74, sext, 2H; 2.16, s, 6H; 2.80, t, 2H; 4.44, q, 2H; 6.71, d, 1H; 7.01, dd, 1H; 7.38, dd, 1H; 7.47, s, 2H; 9.23, s, broad, 1H; 11.10, s, broad, 1H.

EXAMPLE 9

Ethyl ({3,5-dimethyl-4-[(3-isopropyl-1H-indazol-5-yl)oxy]phenyl}amino)(oxo)-acetate

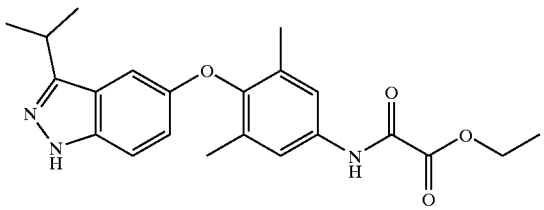

A solution of 56 mg (0.113 mmol) of ethyl [5-(4-{[ethoxy(oxo)acetyl]amino}-2,6-dimethylphenoxy)-3-isopropyl-1H-indazol-1-yl](oxo)acetate in 6 ml of ethanol is treated with a spatula-tipful of sodium ethoxide and stirred at room temperature for 30 min. 5 ml of satd ammonium chloride solution are added, the aqueous phase is extracted 2× with ethyl acetate, and the combined organic phases are washed 1× with water, dried over sodium sulphate and concentrated in vacuo and dried. 28 mc, (63%) of ethyl ({3,5-dimethyl-4-[(3-propyl-1H-indazol-5-yl)oxy]phenyl}amino)(oxo)-acetate are obtained.

300 MHz $^1$H-NMR (DMSO): 1.25, d, 6H; 1.32, t, 3H; 2.07, s, 6H; 3.19, sept., 1H; 4.32, q, 2H; 6.79, d, 1H; 6.97, dd, 1H; 7.42, d, 1H; 7.55, s, 2H; 10.64, s, broad, 1H; 12.49, s, broad, 1H.

EXAMPLE 10

({3,5-Dimethyl-4-[(3-isobutyl-1H-indazol-5-yl)oxy]phenyl}amino)(oxo)acetic acid

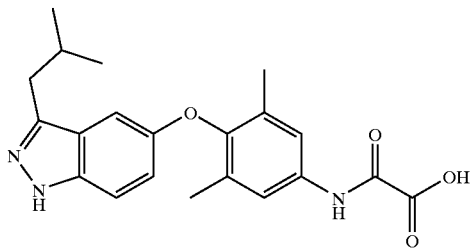

In an analogous manner to the procedure of Example 9, 47 mg (0.092 mmol) of ethyl [5-(4-{[ethoxy(oxo)acetyl]amino}-2,6-dimethylphenoxy)-3-isobutyl-1H-indazol-1-yl](oxo)acetate in 10 ml of ethanol are reacted with a spatula-tipful of sodium ethoxide to give 11 mg (31%) of ({3,5-dimethyl-4-[(3-isobutyl-1H-indazol-5-yl)oxy]phenyl}amino) (oxo)acetic acid.

200 MHz $^1$H-NMR (DMSO): 0.84, d, 6H; 1.95, m, 1H; 2.01, s, 6H; 2.61, d, 2H; 6.71, d, 1H; 6.94, dd, 1H; 7.41, d, 1H; 7.62, s, 2H; 10.27, s, broad, 1H; 12.57, s, broad, 1H.

EXAMPLE 11 AND EXAMPLE 11a

Ethyl ({3,5-dimethyl-4-[(3-pentyl-1H-indazol-5-yl)oxy]phenyl}amino)(oxo)acetate (Example 11) and ({3,5-dimethyl-4-[(3-pentyl-1H-indazol-5-yl)oxy]phenyl} amino)(oxo)acetic acid (Example 11a)

(Example 11)

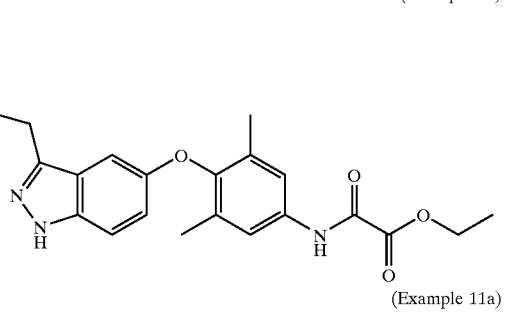

(Example 11a)

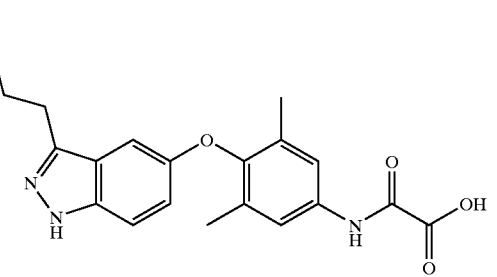

Analogously to the procedure of Example 9, starting from 60 mg (0.115 mmol) of ethyl [5-(4-{bis[ethoxy(oxo)acetyl]amino}-2,6-dimethylphenoxy)-3-pentyl-1H-indazol-1-yl](oxo)acetate in 10 ml of ethanol with a spatula-tipful of sodium ethoxide, 10 mg (21%) of ethyl ({3,5-dimethyl-4-[(3-pentyl-1H-indazol-5-yl)oxy]phenyl}amino)(oxo)acetate (Example 11) and 22 mg (49%) of ({3,5-dimethyl-4-[(3-pentyl-1H-indazol-5-yl)oxy]phenyl}amino)(oxo)acetic acid (Example 11a) are obtained.

EXAMPLE 11

200 MHz $^1$H-NMR (DMSO): 0.80, t, 3H; 1.23, m, 4H; 1.32, t, 3H; 1.62, m, 2H; 2.07, s, 6H; 2.73, t, 2H, 4.31, q, 2H; 6.70, d, 1H; 6.99, dd, 1H; 7.43, d, 1H; 7.57, s, 2H; 10.72, s, broad, 1H; 12,56, s, broad, 1H.

EXAMPLE 11a

200 MHz $^1$H-NMR (DMSO): 0.80, t, 3H; 1.23, m, 4H; 1.61, m, 2H; 2.03, s, 6H; 2.71, t, 2H; 6.69, d, 1H; 6.97, dd, 1H; 7.42, d, 1H; 7.63, s, 2H; 10.36, s, broad, 1H; 10.96, s, broad, 1H; 12.53, s, broad, 1H.

EXAMPLE 12

({3,5-Dimethyl-4-[(3-propyl-1H-indazol-5-yl)oxy]phenyl}amino)(oxo)acetic acid

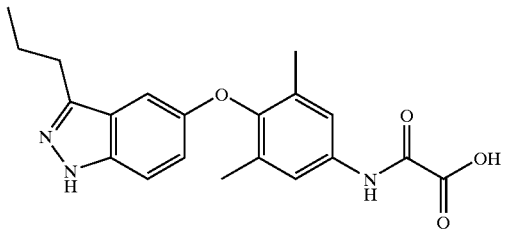

Analogously to the procedure of Example 9, starting from 14 mg (0.028 mmol) of ethyl [5-(4-{[ethoxy(oxo)acetyl]amino}-2,6-dimethylphenoxy)-3-propyl-1H-indazol-1-yl](oxo)acetate in 5 ml of ethanol with a spatula tipful of sodium ethoxide, 6 mg (55%) of ({3,5-dimethyl-4-[(3-propyl-1H-indazol-5-yl)oxy]phenyl}amino)-(oxo)acetic acid are obtained.

300 MHz $^1$H-NMR (DMSO): 0.88, t, 3H; 1.63, m, 2H; 2.03, s, 6H; 2.72, t, 2H; 6.72, d, 1H; 6.96, dd, 1H; 7.40, d, 1H; 7.60, s, 2H; 10.20, s, broad, 1H; 12.52, s, broad, 1H.

EXAMPLE 13

Ethyl ({3,5-dimethyl-4-[(1-tert-butoxycarbonyl-3-pentylindazol-5-yl)oxy]phenyl}-amino)(oxo)acetate

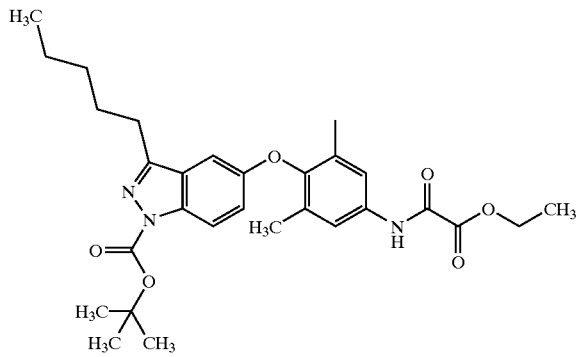

78 mg (0.989 mmol) of pyridine and 166 mg (1.214 mmol) of ethyl oxalyl chloride are added at room temperature to a solution of 381 mg (0.900 mmol) of 1-tert-butoxycarbonyl-5-(4-amino-2,6-dimethylphenoxy)-3-pentylindazole (Example XXIII) in 50 ml of dichloromethane and the reaction mixture is heated under reflux for 2 h after addition. The solvent is subsequently removed in vacuo and the resulting crude product is purified on silica gel using cyclohexane/ethyl acetate 1:1 and methylene chloride. 474 mg (97% of theory) of ethyl ({3,5-dimethyl-4-[(1-tert-butoxycarbonyl-3-pentylindazol-5-yl)oxy]phenyl}amino)(oxo)acetate are obtained.

$^1$H-NMR (200 MHz, DMSO-d$_6$): δ=0.82 (t, 3H), 1.25 (m, 4H), 1.35 (t, 3H), 1.62 (s, 9H), 2.09 (s, 6H), 2.82 (t, 2H), 4.32 (q, 2H), 6.98 (d, 1H), 7.12 (dd, 1H), 7,58 (s, 2H), 7.97 (d, 1H).

EXAMPLE 14

Ethyl ({3,5-dimethyl-4-[(3-pentyl-1H-indazol-5-yl)oxy]phenyl}amino)(oxo)acetate

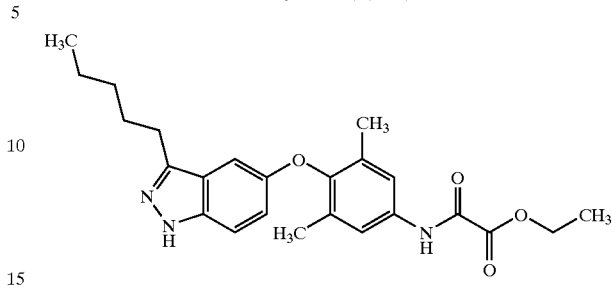

A solution of 474 mg (0.905 mmol) of ethyl ({3,5-dimethyl-4-[(1-tert-butoxycarbonyl-3-pentylindazol-5-yl)oxy]phenyl]}amino)(oxo) acetate (Example 13) and 2.58 g (22.63 mmol) of trifluoroacetic acid in 30 ml of methylene chloride is stirred at room temperature overnight. The mixture is subsequently concentrated in vacuo and the residue obtained is purified on silica gel using cyclohexane/ethyl acetate 3:2. 391 mg (99% of theory) of ethyl-({3,5-dimethyl-4-[(3-pentyl-1H-indazol-5-yl)oxy]phenyl}amino)(oxo)acetate are obtained.

$^1$H-NMR (200 MHz, DMSO-d$_6$): δ=0.80 (t, 3H), 1.23 (m, 4H), 1.32 (t, 3H), 1.62 (m, 2H), 2.07 (s, 6H), 2.73 (t, 2H), 4.31 (q, 2H), 6.70 (d, 1H), 6.99 (dd, 1H), 7,43 (d, 1H), 7.57 (s, 2H), 10.72 (s, broad, 1H), 12.56 (s, broad, 1H).

EXAMPLE 15

Ethyl ({3,5-dimethyl-4-[(1-tert-butoxycarbonyl-3-pentylindazol-5-yl)oxy]phenyl}amino)-acetate

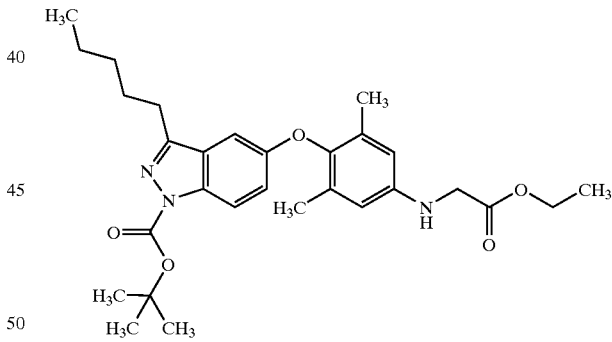

43.4 mg (0.260 mmol) of bromoethyl acetate are added to a solution of 100 mg (0.236 mmol) of 1-tert-butoxycarbonyl-5-(4-amino-2,6-dimethylphenoxy)-3-pentylindazol (Example XXIII) and 26.3 mg (0.260 mmol) of triethylamine in 50 ml of ethanol and the mixture is heated under reflux for 6 h. The mixture is subsequently concentrated in vacuo and the crude product obtained is purified by means of HPLC. 94 mg (71% of theory) of ethyl-({3,5-dimethyl-4-[1-tert-butoxycarbonyl-3-pentylindazol-5-yl)oxy]phenyl}amino)acetate are obtained.

$^1$H-NMR (400 MHz, CDCl$_3$): δ=0.87 (t, 3H), 1.30 (t, 3H), 1.33 (m, 4H), 1.70 (s, 9H), 1.73 (m, 2H), 2.07 (s, 6H), 2.84 (t, 2H), 3.91 (s, 2H), 4.19 (s, broad, 1H), 4.28 (q, 2H), 6.38 (s, 2H), 6.83 (d, 1H), 7.08 (dd, 1H), 7.94 (d, 1H).

EXAMPLE 16

Ethyl ({3,5-dimethyl-4-[(3-pentyl-1H-indazol-5-yl)oxy]phenyl}amino)acetate

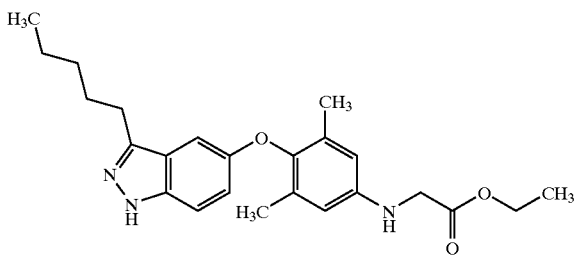

A solution of 100 mg (0.196 mmol) of ethyl-({3,5-dimethyl-4-[1-tert-butoxycarbonyl-3-pentylindazol-5-yl)oxy]phenyl}amino)acetate (Example 15) and 559 mg (4.905 mmol) of trifluoroacetic acid in 30 ml of methylene chloride is stirred at room temperature overnight. The mixture is subsequently concentrated in vacuo and the residue obtained is purified on silica gel using cyclohexane/ethyl acetate 3:1. 16 mg (20% of theory) of ethyl-({3,5-dimethyl-4-[(3-pentyl-1H-indazol-5-yl)oxy]phenyl}amino)acetate are obtained.

$^1$H-NMR (200 MHz, DMSO-$d_6$): δ=0.80 (t, 3H), 1.20 (t, 3H), 1.25 (m, 4H), 1.62 (m, 2H), 1.96 (s, 6H), 2.72 (t, 2H), 3.61 (m, 2H), 3.89 (s, broad, 1H), 6.33 (s, 2H), 6.67 (d, 1H), 6.95 (dd, 1H), 7.39 (d, 1H), 12.45 (s, broad, 1H).

EXAMPLE 17

Methyl-({3,5-dimethyl-4-[(1-tert-butoxycarbonyl-3-pentylindazol-5-yl)oxy]-phenyl}amino)-3-(oxo)propionate

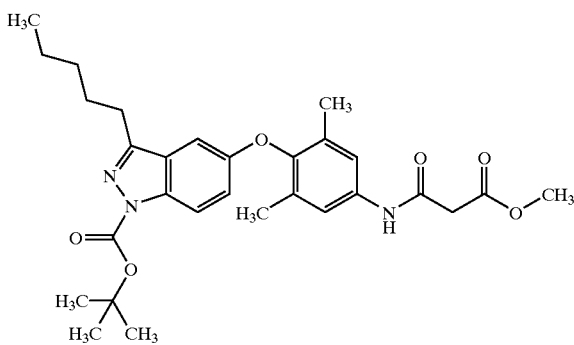

21 mg (0.260 mmol) of pyridine and 35 mg (0.260 mmol) of methyl malonyl chloride are added at room temperature to a solution of 100 mg (0.236 mmol) of 1-tert-butoxycarbonyl-5-(4-amino-2,6-dimethylphenoxy)-3-pentylindazol (Example XXIII) in 50 ml of methylene chloride and the reaction mixture is stirred for 20 min after addition. The solvent is subsequently removed in vacuo and the crude product obtained is purified on silica gel using cyclohexane/ethyl acetate 3:1.90 mg (70% of theory) of methyl-({3,5-dimethyl-4-[(1-tert-butoxy-carbonyl-3-pentylindazol-5-yl)oxy]phenyl}amino)-3-(oxo)propionate are obtained.

$^1$H-NMR (200 MHz, DMSO-$d_6$): δ=0.82 (t, 3H), 1.27 (m, 4H), 1.62 (s, 9H), 1.64 (m, 2H), 2.06 (s, 6H), 2.73 (t, 2H), 3.48 (s, 2H), 3.68 (s, 3H), 6.97 (d, 1H), 7.12 (dd, 1H), 7.40 (s, 2H), 7.97 (d, 1H), 10.17 (s, broad, 1H).

EXAMPLE 18

Methyl-({3,5-dimethyl-4-[(3-pentyl-1H-indazol-5-yl)oxy]phenyl}amino)-3-(oxo)-propionate

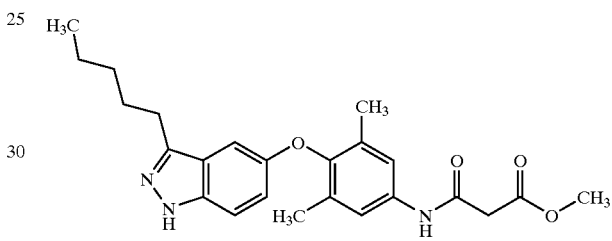

A solution of 74 mg (0.141 mmol) of ethyl-({3,5-dimethyl-4-[1-tert-butoxycarbonyl-3-pentylindazol-5-yl)oxy]phenyl}amino)-3-(oxo)propionate (Example 17) and 403 mg (3.533 mmol) of trifluoroacetic acid in 30 ml of methylene chloride is stirred at room temperature overnight. The mixture is subsequently concentrated in vacuo and the residue obtained is purified on silica gel using cyclohexane/ethyl acetate 1:1. 58 mg (93% of theory) of methyl-({3,5-dimethyl-4-[(3-pentyl-1H-indazol-5-yl)oxy]phenyl}amino)-3-(oxo)propionate are obtained.

$^1$H-NMR (300 MHz, DMSO-$d_6$): δ=0.81 (t, 3H), 1.24 (m, 4H), 1.62 (m, 4H), 2.04 (s, 6H), 2.73 (t, 2H), 3.47 (s, 2H), 3.68 (s, 3H), 6.68 (d, 1H), 6.97 (dd, 1H), 7.38 (s, 2H), 7.42 (d, 1H), 10.14 (s, 1H).

---

What is claimed is:

1. Compounds of the general formula (I),

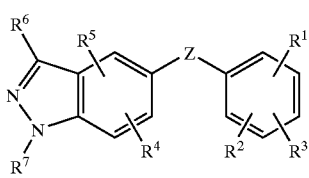

(I)

in which
Z represents O, S, $CH_2$, CHF or $CF_2$,
$R^1$ and $R^2$ are identical or different and represent hydrogen, halogen, $(C_1-C_6)$-alkyl, $CF_3$, $CHF_2$, $CH_2F$, vinyl or $(C_3-C_7)$-cycloalkyl, where at least one of the two substituents is not equal to hydrogen and is in the ortho position relative to the bridge bond,
$R^3$ represents a group of the formula $A(CH_2)_n$—$(CO)_m R^8$, in which A represents $CH_2$, O, S, CO or $NR^9$, in which $R^9$ denotes hydrogen, $(C_1-C_6)$-alkyl or $(C_3-C_8)$-cycloalkyl or represents the group —$(CH_2)_n$—$(CO)_m$—O-$(C_1-C_4)$-alkyl,
n represents the numbers 0 to 3,
m represents the number 0, 1 or 2,
$R^8$ represents hydrogen, $OR^{10}$, $NR^{11}R^{12}$, $(C_1-C_8)$-alkyl, $(C_3-C_8)$-cycloalkyl, $(C_6-C_{10})$-aryl, or a saturated, unsaturated or aromatic 5-to 10-membered heterocycle having up to four identical or different heteroatoms from the series S, O and/or N, where the abovementioned radicals are optionally substituted by one, two or three, identical or different substituents from the group halogen, hydroxyl, cyano, nitro, amino, $CF_3$, $(C_1-C_6)$-alkyl, $(C_1-C_6)$-alkoxy, $(C_3-C_8)$-cycloalkyl, —OCO—$R^{13}$, —CO—O—$R^{14}$, —CO—$NR^{15}R^{16}$, —$NHCOR^{17}$ or $NHCOOR^{17}$, where $R^{10}$, $R^{11}$, $R^{12}$, $R^{13}$, $R^{14}$, $R^{15}$, $R^{16}$ and $R^{17}$ are identical or different and in each case represent hydrogen, phenyl, benzyl, $(C_1-C_6)$-alkyl, $(C_1-C_6)$-alkoxy or $(C_3-C_8)$-cycloalkyl, which for their part are optionally mono- or polysubstituted by halogen, hydroxyl, amino, $(C_1-C_4)$-alkoxy, —CO—O $(C_1-C_4)$-alkyl, —NH—CO—O$(C_1-C_4)$-alkyl, —O—CO—$(C_1-C_4)$-alkyl, a heterocycle or optionally halogen- or hydroxyl-substituted phenyl, $R^4$ and $R_5$ are identical or different and in each case represent hydrogen, hydroxyl, halogen, cyano, intro, $(C_1-C_4)$-alkyl, or the radical of the formula $NR^{18}R^{19}$, where $R^{18}$ and $R^{19}$ have the meaning indicated for $R^{10}$ and can be identical to or different from this substituent, $R^6$ represents halogen or has the meaning indicated for $R^8$ and is identical to or different from this substituent or represents the radical

in which $R^{20}$ and $R^{21}$ together represent oxygen, or are each identical or different and represent hydrogen, halogen, hydroxy, $(C_1-C_6)$-alkyl, $(C_1-C_6)$-alkoxy or the radical —$NR^{15}R^{16}$ and $R^{22}$ has the meaning of $R^8$ and is identical to or different from this, $R^7$ represents hydrogen or an acyl group and their salts.

2. Compounds of the general formula (I) according to claim 1

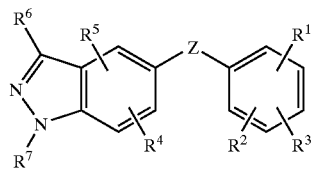

in which

Z represents O, $CH^2$ or $CF^2$, $R^1$ and $R^2$ are identical or different and represent hydrogen, fluorine, chlorine, bromine, $(C_1-C_4)$-alkyl, $CF_3$, $CHF_2$, $CH_2F$, vinyl or $(C_3-C_6)$-cycloalkyl, where at least one of the two substituents is not equal to hydrogen and is in the ortho position relative to the bridge bond, in particular both substituents are not equal to hydrogen and both are in the ortho position, $R^3$ represents a group of the formula A-$(CH_2)_n$—$(CO)_m R^8$, in which A represents $CH_2$, O or $NR^9$, in which $R^9$ denotes hydrogen, $(C_1-C_4)$-alkyl or $(C_3-C_7)$-cycloalkyl or represents the group —$(CH_2)_n$—$(CO)_m$—O-$(C_1-C_4)$-alkyl, n represents the number 0 or 1, m represents the number 1 or 2, $R^8$ represents hydrogen, $OR^{10}$, $NR^{11}R^{12}$, $(C_1-C_8)$-alkyl, $(C_3-C_8)$-cycloalkyl, $(C_6-C_{10})$-aryl, or a saturated, unsaturated or aromatic 5- to 10-membered heterocycle having up to four identical or different heteroatoms from the series S, O and/or N, where the above-mentioned hydrocarbon radicals and heterocycles are optionally substituted by one, two or three identical or different substituents from the group halogen, hydroxyl, cyano, nitro, amino, $CF_3$, $(C_1-C_4)$-alkyl, $(C_1-C_4)$-alkoxy, $(C_1-C_4)$-alkoxyphenyl, $(C_3-C_8)$-cycloalkyl, —O—CO—$R^{13}$, —CO—O—$R^{14}$, —CO—$NR^{15}R^{16}$, —$NHCOR^{17}$ or —$NHCOOR^{17}$, where $R^{10}$, $R^{11}$, $R^{12}$, $R^{13}$, $R^{14}$, $R^{15}$, $R^{16}$ and $R^{17}$ are identical or different and each represent hydrogen, benzyl, $(C_1-C_6)$-alkyl or $(C_3-C_8)$-cycloalkyl, which for their part are optionally mono- or polysubstituted by fluorine, chlorine, hydroxyl, amino, —CO—O-$(C_1-C_4)$-alkyl, —NH—CO—O$(C_1-C_4)$-alkyl, —O—CO-$(C_1-C_4$-alkyl, imidazolyl, hydroxyphenyl or $(C_1-C_4)$-alkoxy, $R^4$ and $R^5$ are identical or different and each represent hydrogen, halogen or $(C_1-C_4)$-alkyl, $R_6$ represents chlorine, fluorine, bromine or has the meaning indicated for $R^8$ and is identical to or different from this abovementioned substituent or represents the radical

in which $R^{20}$ and $R^{21}$ together represent oxygen, or are each identical or different and represent hydrogen, halogen, hydroxyl, $(C_1-C_4)$-alkyl, $(C_1-C_4)$-alkoxy or the radical —$NR^{15}R^{16}$ and $R^{22}$ has the meaning of $R^8$ and is identical to or different from this, $R^7$ represents hydrogen, and their salts.

3. Compounds of the general formula (I) according to claim 1 in which

Z represents $CH_2$ or oxygen, $R^1$ and $R^2$ are identical or different and represent methyl, ethyl, propyl, isopropyl, chlorine, bromine, $CF_3$, vinyl or cyclopropyl, where both substituents are in the ortho position to the bridge bond, $R^3$ represents the group —O—$(CH_2)_n$—CO—$R^8$ or the group $NR^9(CH_2)_n$—$(CO)_m R^8$, which is each in the para position relative to the bridge bond, where m represents the number 1 or 2, n represents the number 1 or 0, $R^9$ denotes substituted $(C_1-C_4)$-alkyl, $(C_3-C_7)$-cycloalkyl, or hydrogen, $R^8$ represents methyl, ethyl, n-propyl, isopropyl, n-, i-, s- or t-butyl, n-pentyl or n-hexyl, thiophenyl, pyridyl, or the groups —$CH_2$—O—benzyl, $OR^{10}$ or $NR^{11}R^{12}$, where $R^{10}$ represents hydrogen, or optionally hydroxyl-substituted straight-chain or branched alkyl having up to 7 carbon atoms, where $R^{11}$ and $R^{12}$ are identical or different and represent hydrogen, cyclopropyl, cyclobutyl, cyclopentyl, cyclohexyl, cycloheptyl, methoxy, ethoxy, n-propoxy, isopropoxy, t-butoxy, n-pentoxy, n-hexoxy or straight-chain or branched alkyl having up to 6 carbon atoms, where alkyl for its part is optionally mono- or polysubstituted identically or differently by hydroxyl, —CO—O$(C_1-C_4)$-alkyl, —NH—CO—O $(C_1-C_4)$-alkyl, imidazolyl and/or hydroxyphenyl, R⁴ and R⁵ represent methyl, fluorine or chlorine or hydrogen, R⁶ represents hydrogen, OR¹⁰, NR¹¹R¹², methyl, ethyl, n-propyl, isopropyl n-, i-, s- or t-butyl, n-pentyl, (C₃–C₆)-cycloalkyl, (C₆–C₁₀)-aryl, or represents a saturated, unsaturated or aromatic 5- to 10-membered heterocycle having up to three identical or different heteroatoms from the series S, O and/or N, where the abovementioned hydrocarbon radicals and heterocycles are optionally substituted by one, two or three identical or different substituents from the group halogen, hydroxyl, cyano, nitro, amino, CF₃, (C₁–C₄)-alkyl, (C₁–C₄)-alkoxy, (C₃–C₈)-cycloalkyl, O—CO—R¹³, —CO—O—R¹⁴, —CO—NR¹⁵R¹⁶ or —NHCOOR¹⁷, where R¹⁰, R¹¹, R¹², R¹³, R¹⁴, R¹⁵, R¹⁶ and are identical or different and each represent hydrogen, benzyl, (C₁–C₄)-alkyl or (C₃–C₆)-cycloalkyl, which for their part are optionally substituted by amino or (C₁–C₄)-alkoxy, or represents the radical

in which

R²⁰ and R²¹ together represent oxygen, or are each identical or different and represent hydrogen, halogen, hydroxyl, (C₁–C₄)-alkyl, (C₁–C₄)-alkoxy or the radical —NR¹⁵R¹⁶ and R²² represents hydrogen, OR¹⁰, NR¹¹R¹², (C₁–C₄)-alkyl, (C₃–C₆)-cycloalkyl, (C₆–C₁₀)-aryl, or a saturated, unsaturated or aromatic 5- to 10-membered heterocycle having up to three identical or different heteroatoms from the series S, O and/or N, where the abovementioned hydrocarbon radicals and heterocycles are optionally substituted by one, two or three identical or different substituents from the group halogen, hydroxyl, cyano, nitro, amino, CF₃, (C₁–C₄)-alkyl, (C₁–C₄)-alkoxy, (C₃–C₈)-cycloalkyl, O—CO—R¹³, —CO—O—R¹⁴, —CO—NR¹⁵R¹⁶ or —NHCOOR¹⁷, where R¹⁰, R¹¹, R¹², R¹³, R¹⁴, R¹⁵, R¹⁶ and R¹⁷ are identical or different and each represent hydrogen, benzyl, (C₁–C₄)-alkyl or (C₃–C₆)-cycloalkyl, which for their part are optionally substituted by amino or (C₁–C₄)-alkoxy, R⁷ represents hydrogen, and their salts.

4. Process for the preparation of compounds of the general formula (I) according to claim 1, characterized in that reactive indazole derivatives of the general formula (II) are reacted with reactive phenyl derivatives of the general formula (III)

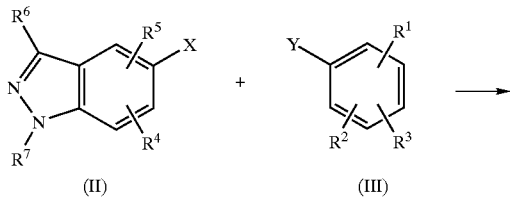

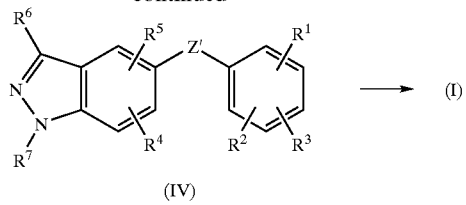

where the substituents R¹, R², R⁴, R⁵, R⁶ and R⁷ have the meaning indicated in claim 1 and R³' has the meaning indicated for R³ in claim 1 or represents NO₂ or NPG, where PG is a protective group, X and Y each represent groups of opposite reactivity, Z' has the meaning indicated for Z in claim 1 or represents

if appropriate in the presence of inert solvents and catalysts and if appropriate with isolation of the intermediates of the general formula (IV), or directly to give compounds of the formula (I).

5. Medicament comprising at least one compound of the general formula (I) according to claim 1 and a pharmaceutically acceptable carrier.

6. Process for the production of medicaments, characterized in that at least one compound of the general formula (I) according to claim 1 is converted into a suitable administration form using excipients and carriers.

7. A method of treating arteriosclerosis and hypocholesterolaemia, comprising administering to a mammal an effective amount of a compound according to claim 1.

8. A method of treating forms of disease which can be treated using natural thyroid hormone, comprising administering to a mammal an effective amount of a compound according to claim 1.

9. The compound of claim 1, wherein R⁷ is acetyl.

10. The compound of claim 2, wherein A-(CH₂)ₙ—(CO)ₘ—R⁸ is in the para position relative to the bridge bond.

11. The compound of claim 3, wherein Z represents oxygen.

12. The compound of claim 3, wherein R³ is NR⁹—(CH₂)ₙ—(CO)ₘR⁸.

13. The compound of claim 3, wherein m represents the number 2.

14. The compound of claim 3, wherein R⁹ is —CH₂—CO—O-(C₁–C₄)-alkyl or —CO—CO—O-(C₁–C₄)-alkyl.

15. The compound of claim 3, wherein R⁹ is hydrogen.

16. The compound of claim 3, wherein R⁴ and R⁵ represent hydrogen.

17. The process of claim 4 wherein X is an electrophilic radical which reacts with a nucleophilic Y substituent or X is a nucleophilic substituent which reacts with an electrophilic Y radical.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Homo sapiens

<400> SEQUENCE: 1
gggaatcgac tccgaggtc
```

```
<210> SEQ ID NO 2
<211> LENGTH: 20
<212> TYPE: DNA
<213> ORGANISM: Homo sapiens

<400> SEQUENCE: 2
gatcttggtg aaacgcacga                                              20

<210> SEQ ID NO 3
<211> LENGTH: 23
<212> TYPE: DNA
<213> ORGANISM: Homo sapiens

<400> SEQUENCE: 3
acaagacggc ccgtgcacta cgc                                          23

<210> SEQ ID NO 4
<211> LENGTH: 20
<212> TYPE: DNA
<213> ORGANISM: Homo sapiens

<400> SEQUENCE: 4
cgaggtgctg gaggaatacc                                              20

<210> SEQ ID NO 5
<211> LENGTH: 21
<212> TYPE: DNA
<213> ORGANISM: Homo sapiens

<400> SEQUENCE: 5
ctagccggtc aatagccaca g                                            21

<210> SEQ ID NO 6
<211> LENGTH: 22
<212> TYPE: DNA
<213> ORGANISM: Homo sapiens

<400> SEQUENCE: 6
catgatgcgg cgtgcctttg ag                                           22
```